(12) United States Patent
Bolli et al.

(10) Patent No.: US 6,720,322 B2
(45) Date of Patent: Apr. 13, 2004

(54) BUTYNE DIOL DERIVATIVES

(75) Inventors: Martin Bolli, Allschwil (CH);
Christoph Boss, Allschwil (CH);
Martine Clozel, Binningen (CH);
Walter Fischli, Allschwil (CH)

(73) Assignee: Actelion Pharamceuticals Ltd., Allschwil (CH)

( * ) Notice: Subject to any disclaimer, the term of this patent is extended or adjusted under 35 U.S.C. 154(b) by 55 days.

(21) Appl. No.: 10/168,752

(22) PCT Filed: Dec. 14, 2000

(86) PCT No.: PCT/EP00/12743
§ 371 (c)(1),
(2), (4) Date: Jun. 24, 2002

(87) PCT Pub. No.: WO01/46156
PCT Pub. Date: Jun. 28, 2001

(65) Prior Publication Data
US 2003/0087920 A1 May 8, 2003

(30) Foreign Application Priority Data
Dec. 22, 1999 (WO) ................................ PCT/EP99/10276

(51) Int. Cl.[7] .................. A61K 31/5377; A61K 31/506; C07D 401/14; C07D 413/14
(52) U.S. Cl. .................... 514/235.8; 544/123; 544/296; 544/298; 544/319
(58) Field of Search ................................ 544/123, 296, 544/298, 319; 514/235.8

(56) References Cited

U.S. PATENT DOCUMENTS 6,596,719 B1 * 7/2003 Bolli et al. ................. 544/319

FOREIGN PATENT DOCUMENTS

EP 0 743 307 11/1996
EP 0 768 304 4/1997

OTHER PUBLICATIONS

Bolli et al, *ChemAbstracts*, vol. 139, No. 162, 651 (2003).*
Ichikizaki et al. The preparation of 4–methoxy–2–butenal, a new dienophile and notes on related compouonds. Bull. Chem. Soc. Japan 1955, 28:80–83.
Advanced Organic Chemistry by J. March 3rd Ed. Wiley, 1985, p. 803.

* cited by examiner

*Primary Examiner*—Robert W. Ramsuer
(74) *Attorney, Agent, or Firm*—Pennie & Edmonds LLP

(57) ABSTRACT

The present invention relates to novel butyne diol derivatives of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin receptor antagonists.

10 Claims, No Drawings

BUTYNE DIOL DERIVATIVES

This is a national stage application of International Application PCT/EP00/12743, filed Dec. 14, 2000, which was published under PCT Article 21(2) as PCT Publication No. WO 01/46156 in English, and which claims the benefit of International Application PCT/EP99/10276 filed Dec. 22, 1999. Both International Applications PCT/EP00/12743 and PCT/EP99/10276 are hereby incorporated by reference in their entireties.

The present invention relates to novel butyne diol derivatives of the general formula I and their use as active ingredients in the preparation of pharmaceutical compositions. The invention also concerns related aspects including processes for the preparation of the compounds, pharmaceutical compositions containing one or more compounds of the general formula I and especially their use as endothelin receptor antagonists.

Endothelins (ET-1, ET-2, and ET-3) are 21-amino acid peptides produced and active in almost all tissues (Yanagisawa M et al.: Nature (1988) 332:411. Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi G M et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the 3 endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, no endothelin receptor antagonist is marketed yet, several are in clinical trials. However, these molecules possess a number of weaknesses such as complex synthesis, low solubility, high molecular weight, poor pharmacokinetics or safety problems (e.g. liver enzyme increases). Furthermore, the contribution of differential $ET_A/ET_B$ receptor blockade to the clinical outcome is not known. Thus, tailoring of the physicochemical, pharmacokinetic properties and the selectivity profile of each antagonist for a given clinical indication is mandatory. We have discovered a new class of butyne-diol derivatives of the structure below and found that they allow the specific tailoring described above.

The inhibitory activity of the compounds of formula I on endothelin receptors can be demonstrated using the test procedures described hereinafter:

For the evaluation of the potency and efficacy of the compounds of the general formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After two h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of formula I are given in Table 1

TABLE 1

| | $IC_{50}$[nM] | |
|---|---|---|
| Compound of | $ET_A$ | $ET_B$ |
| Example 1g | 26 | 77 |
| Example 2c | 126 | 44 |
| Example 3e | 22 | 1520 |
| Example 4d | 53 | 2030 |
| Example 5b | 38 | 635 |
| Example 9d | 16 | 49 |
| Example 11d | 49 | 97 |
| Example 18 | 79 | 36 |
| Example 19 | 112 | 45 |
| Example 21 | 230 | 44 |
| Example 58 | 7 | 123 |
| Example 70 | 94 | 375 |
| Example 71 | 13 | 28 |
| Example 72 | 1 | 42 |
| Example 81 | 1 | 197 |
| Example 84 | 2 | 241 |
| Example 89 | 13 | 1140 |
| Example 94 | 13 | 107 |

2) Inhibition of Endothelin-induced Contractions on Isolated Rat Aortic Rings ($ET_A$ Receptors) and Rat Tracheal Rings ($ET_B$ Receptors)

The functional inhibitory potency of the endothelin antagonists was assessed by their inhibition of the contraction induced by endothelin-1 on rat aortic rings ($ET_A$ receptors) and of the contraction induced by sarafotoxin S6c on rat tracheal ($ET_B$ receptors). Adult Wistar rats were anesthetized and exsanguinated. The thoracic aorta or trachea were excised, dissected and cut in 3–5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, $MgSO_4$ 1.2, $KH_2PO_4$ 1.5, $NaHCO_3$ 25, $CaCl_2$ 2.5, glucose 10) keep at 37° C. and gassed with 95% $O_2$ and 5% $CO_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the $EC_{50}$ induced by different concentrations of test compound. $EC_{50}$ is the concentration of endothelin needed to get a half-maximal contraction, $pA_2$ is the negative logarithm of the antagonist concentration which induces a two-fold shift in the $EC_{50}$ value.

The $pA_2$ values obtained with compounds of formula I are given in Table 2.

TABLE 2

| Compound of | $pA_2$ | |
| --- | --- | --- |
| | aortic rings | trachea |
| Example 4d | 7.15 | 5.89 |
| Example 9d | 7.11 | 6.47 |
| Example 11d | 7.05 | 7.03 |
| Example 19 | <5 | 7.62 |
| Example 58 | 7.57 | |
| Example 59 | 7.70 | |
| Example 72 | 7.70 | |
| Example 81 | 7.56 | |
| Example 84 | 8.11 | |

Because of their ability to inhibit the endothelin binding, the described compounds can be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, as well as other diseases presently known to be related to endothelin.

The compounds can be administered orally, rectally, parenterally, e.g. intravenously, intramuscularly, subcutaneously, intrathecally or transdermally; or sublingually or as ophthalmic preparation or administered as aerosol. Examples of applications are capsules, tablets, oral administered suspensions or solutions, suppositories, injections, eye-drops, ointments or aerosols/nebulizers.

Preferred applications are intravenous, intra-muscular, eye drops or oral administrations. The dosage used depends upon the type of the specific active ingredient, the age and the requirements of the patient and the kind of application. Generally, dosages of 0.1–50 mg/kg body weight per day are considered. The preparations with compounds can contain inert or as well pharmacodynamically active excipients. Tablets or granules, for example, could contain a number of binding agents, filling excipients, carrier substances or diluents.

In the Patent Specifications EP 743307 and EP 882719 related endothelin receptor antagonists are disclosed. However, only in EP 882719 in Table 1 $IC_{50}$ values for the $ET_A$ receptor are given. The corresponding values of the instantly claimed compounds are in a head-to-head comparison much better and also much more specific, since one can differentiate between activity of both receptors and can also prepare mixed antagonists.

The present invention relates to butyne diol derivatives of the general formula I, general formula I

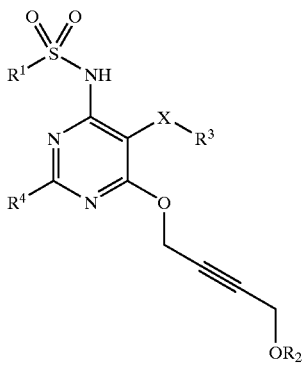

wherein $R^1$ represents phenyl; mono-, di- or tri-substituted phenyl substituted with halogen, lower alkyl, lower alkenyl, lower alkynyl, lower alkoxy, hydroxy-lower alkyl, hydroxy-lower alkenyl, hydroxy-lower alkynyl, trifluoromethyl, cycloalkyl, hydroxy-cycloalkyl; 2-pyridyl; 5-substituted 2-pyridyl substituted with lower alkyl, five membered heteroaryl rings containing one or two nitrogen, sulfur or oxygen atoms;

$R^2$ represents hydrogen; lower alkyl; phenyl; mono-, di- or tri-substituted phenyl substituted with halogen, lower alkyl, lower alkoxy, lower alkyloxy-lower alkyl, trifluoromethyl, five membered heteroaryl rings containing one or two nitrogen, sulfur or oxygen atoms which may be mono- or di-substituted with halogen, lower alkyl, lower alkoxy; benzyl; mono- or di-substituted benzyl substituted with halogen, lower alkyl, lower alkoxy, trifluoromethyl, 2-pyridyl; mono- or di-substituted 2-pyrimidyl substituted with lower alkyl, lower alkoxy, halogen, trifluoromethyl, a group of the formula —C(A)—B—$R^a$, wherein A represents O or S;

B represents NH and $R^a$ represents lower alkyl; cycloalkyl; phenyl; mono-, di- or tri-substituted phenyl substituted with halogen, lower alkyl, lower alkenyl, lower alkoxy, trifluoromethyl, six membered heteroaryl rings containing one or two nitrogen atoms which may be mono-, di- or substituted with halogen, lower alkyl, lower akyloxy;

$R^3$ represents phenyl; mono-, di- or tri-substituted phenyl substituted with lower alkyl, lower alkenyl, lower alkyloxy, trifluoromethyl, halogen, hydroxy;

$R^4$ represents hydrogen, halogen, trifluoromethyl, lower alkyl, lower alkyloxy, lower alkylthio, lower alkyl-oxy-lower alkyl; phenyl; mono- or di-substituted phenyl substituted with halogen, lower alkyl, lower alkoxy, lower alkylen or lower alkenylen or lower alkylenoxy or lower alkylendioxy forming with the phenyl ring a five- or six-membered ring, heteroaryl; heterocyclyl;

X represents oxygen; sulfur; or a bond;

and pure enantiomers, enantiamerically pure diastereomers, mixtures of diastereomers, diastereomeric racemates, mixtures of diastereomeric racemates and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec-butyl, tert.-butyl, pentyl, hexyl, heptyl, methoxy, ethoxy, propoxy, butoxy, iso-butoxy, sec-butoxy and tert.-butoxy. Lower alkylendioxy-groups are preferably methylen-dioxy, ethylen-dioxy, propylen-dioxy and butylen-dioxy-groups. Examples of lower alkanoyl-groups are acetyl, propanoyl and butanoyl. Lower alkenylen means e.g.vinylen, propenylen and butenylen. Lower alkenyl and lower alkynyl means groups like ethylen, propylen, butylen, tert.-butylen(2-methyl-propenyl), and acetylenyl, propinylen, butinylen, pentinylen, 2-methyl-pentinylen etc. Lower alkenyloxy means allyloxy, vinyloxy, propenyloxy and the like. The expression cycloalkyl means a saturated cyclic hydrocarbon ring with 3 to 6 carbon atoms, e.g. cyclopropyl, cyclobutyl, cyclopentyl and cyclohexyl which may be substituted with lower alkyl, hydroxy-lower alkyl, amino-lower alkyl, lower alkoxy-lower alkyl and lower alkenylen groups. The expression heterocyclyl means saturated or unsaturated (but not aromatic) five-, six- or seven-membered rings containing one or two nitrogen, oxygen or sulfur atoms which may be the same or different and which rings may be substituted with lower alkyl, amino, halogen, nitro, hydroxy, lower alkoxy, e.g. piperidinyl, morpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl etc. and substituted derivatives of such rings with substituents as outlined above. The expression heteroaryl means six-membered aromatic rings containing one to four nitrogen atoms, benzofused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containig an oxygen and nitrogen atom and benzo fused derivatives thereof, five membred aromatic rings containing a sulfur, nitrogen or oxygen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring, e.g. furanyl, thienyl, pyrrolyl, pyridinyl, indolyl, quinolinyl, isoquinolinyl, imidazolyl, triazinyl, thiazinyl, pyridazinyl, oxazolyl, etc. whereby such rings may be substituted with lower alkyl, amino, amino-lower alkyl, halogen, hydroxy, lower alkoxy or trifluoromethyl. The expression aryl represents mono-, di- or tri-substituted aromatic rings with 6 to 10 carbon atoms like phenyl or naphthyl rings which may be substituted with phenyl, halogen, hydroxy, lower alkoxy, lower alkyl, trifluoromethyl, lower alkenyloxy, trifluoromethoxy, cyclopropyl, hydroxy-cyclopropyl, lower alkylenoxy or lower alkylendioxy.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide etc.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates. The present invention encompasses all these forms. Mixtures may be separated in a manner known per se, i.e. by column chromatography, thin layer chromatography, HPLC, crystallization etc.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension and pulmonary hypertension. They can also be used for atherosclerosis, prevention of restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, as well as other diseases presently known to be related to endothelin.

These compositions may be administered in enteral or oral form e.g. as tablets, dragees, gelatine capsules, emulsions, solutions or suspensions, in nasal form like sprays or rectically in form of suppositories. These compounds may also be administered in intramuscular, parenteral or intraveneous form, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols etc. may be used. For the preparation of solutions and sirups e.g. water, polyols, saccharose, glucose etc. are used. Injectables are prepared by using e.g. water, polyols, alcohols, glycerin, vegetable oils, lecithin, liposomes etc. Suppositories are prepared by using natural or hydrogenated oils, waxes, fatty acids (fats), liquid or half-liquid polyols etc.

The compositions may contain in addition preservatives, stabilisation improving substances, viscosity improving or regulating substances, solubility improving substances, sweeteners, dyes, taste improving compounds, salts to change the osmotic pressure, buffer, antioxidants etc.

The compounds of formula I may also be used in combination with one or more other therapeutically useful substances e.g. α- and β-blockers like Phentolamine, Phenoxybenzamine, Atenolol, Propranolol, Timolol, Metoprolol, Carteolol etc.; Vasodilators like Hydralazine, Minoxidil, Diazoxide, Flosequinan etc.; Calcium-antagonists like Diltiazem, Nicardipine, Nimodipine, Verapamil, Nifedipine etc.; ACE-inhibitors like Cilazapril, Captopril, Enalapril, Lisinopril etc.; Potassium activators like Pinacidil etc. Angiotensin II antagonists; Diuretics like Hydrochlorothiazide, Chlorothiazide, Acetolamide, Bumetamide, Furosemide, Metolazone, Chlortalidone etc.; Sympatholitics like Methyldopa, Clonidine, Guanabenz, Reserpine etc.; and other therapeutics which serve to treat high blood pressure or any cardiac disorders.

The dosage may vary within wide limits but should be adapted to the specific situation. In general the dosage given in oral form should daily be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

A preferred group of compounds are compounds of formula I wherein $R^1$, $R^2$, and $R^4$ are as defined above, and wherein $R^3$ represents phenyl; mono substituted phenyl substituted with lower alkyl, lower alkyloxy, trifluoromethyl, halogen;

X represents oxygen or a single bond, and pharmaceutically acceptable salts thereof.

Another preferred group of compounds are compounds of formula II formula II

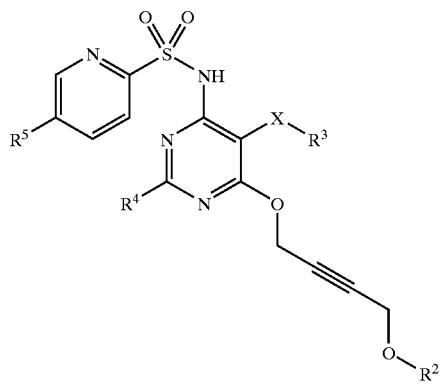

wherein $R^2$, $R^3$, $R^4$, and X are as defined in formula I above, and $R^5$ represents lower alkyl, and pharmaceutically acceptable salts of compounds of formula II.

Another group of preferred compounds are compounds of formula III formula III

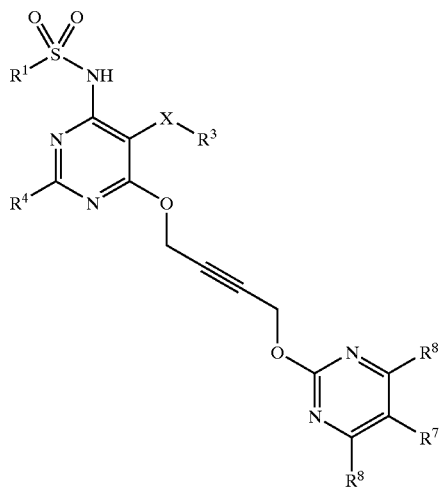

wherein $R^1$, $R^3$, $R^4$, and X are as defined in formula I above, and $R^6$, $R^7$, and $R^8$, each and independently represents hydrogen, lower alkyl, lower alkyloxy, halogen, trifluoromethyl;

and pharmaceutically acceptable salts thereof.

Yet another group of preferred compounds are compounds of formula IV formula IV

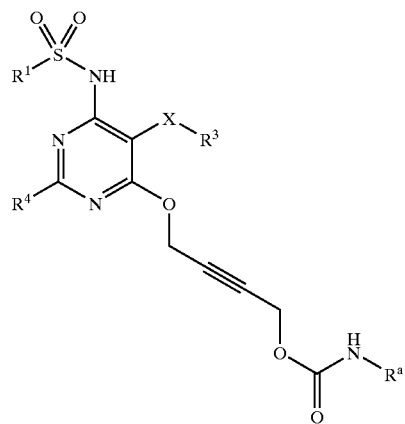

wherein $R^1$, $R^3$, $R^4$, $R^a$ and X are as defined in formula I above, and pharmaceutically acceptable salts thereof.

Another group of preferred compounds are compounds of formula I wherein $R^1$, $R^3$, $R^4$, and X are as defined in formula I above, and wherein $R^2$ represents lower alkyl, and pharmaceutically acceptable salts thereof.

Another group of preferred compounds are the compounds given below:

5-isopropyl-N-[6-(4-hydroxy-2-butynyloxy)-5-(o-methoxyphenoxy)-2-(4-pyridyl)-4-pyrimidinyl]-2-pyridine sulfonamide;

4-tert.-butyl-N-[6-(4-hydroxy-2-butynyloxy)-5-(o-methoxyphenoxy)-2-(4-pyridyl)-4-pyrimidinyl]-benzene sulfonamide;

5-methyl-N-[6-(4-hydroxy-2-butynyloxy)-5-(o-methoxyphenoxy)-2-(4-pyridyl)-4-pyrimidinyl]-2-pyridine sulfonamide;

5-isopropyl-N-[6-chloro-5-(o-methoxyphenoxy)-2-(2-pyrimidinyl)-4-pyrimidinyl]-2-pyridine sulfonamide;

4-tert.-butyl-N-[6-chloro-5-(o-methoxyphenoxy)-2-(2-pyrimidinyl)-4-pyrimidinyl]benzene sulfonamide;

5-isopropyl-N-[6-(4-hydroxy-2-butynyloxy)-5-(o-methoxyphenoxy)-2-(N-morpholino)-4-pyrimidinyl]-2-pyridine sulfonamide;

5-isopropyl-N-[6-(4-hydroxy-2-butynyloxy)-5-(p-tolyl)-2-(4-pyridyl)-4-pyrimidinyl]-2-pyridine sulfonamide;

5-isopropyl-N-[6-(4-(4,6-dimethoxy-2-pyrimidinyloxy)-2-butynyloxy)-5-(o-methoxyphenoxy)-2-(4-pyridyl)-4-pyrimidinyl]-2-pyridine sulfonamide;

4-tert.-butyl-N-[6-(4-(2-pyrimidinyloxy)-2-butynyloxy)-5-(o-methoxyphenoxy)-2-(4-pyridyl)-4-pyrimidi-nyl]-benzene sulfonamide;

4-tert.-butyl-N-[6-(4-(4,6-dimethoxy-2-pyrimidinyloxy)-2-butynyloxy)-5-(o-methoxyphenoxy)-2-(4-pyridyl)-4-pyrimidinyl]-benzene sulfonamide;

2-pyridinyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester;

phenyl-carbamic acid 4-[6-(5-isopropyl-pyridine-2-sulfonylamino)-5-(2-methoxy-phenoxy)-2-methyl-pyrimidin-4-yloxy]-but-2-ynyl ester;

phenyl-carbamic acid 4-[6-(5-isopropyl-pyridine-2-sulfonylamino)-5-(2-methoxy-phenoxy)-2-morpholin-4-yl-pyrimidin-4-yloxy]-but-2-ynyl ester;

2-pyridinyl-carbamic acid 4-[6-(5-isopropyl-pyridine-2-sulfonylamino)-5-(2-methoxy-phenoxy)-2-(N-morpholino)-pyrimidin-4-yloxy]-but-2-ynyl ester;

2-pyridinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester;

4-pyrazinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester;

4-tert.-butyl-N-[6-(4-methoxy-2-butynyloxy)-5-(o-methoxy-phenoxy)-2-(2-pyrimidinyl)-4-pyrimidinyl] benzene sulfonamide;

5-isopropyl-N-[6-(4-methoxy-2-butynyloxy)-5-(o-methoxyphenoxy)-2-(N-morpholino)-4-pyrimidinyl]-2-pyridine sulfonamide;

and pharmaceutically acceptable salts thereof.

The compounds of the general formula I are prepared from compounds of the formula V by one of the two pathways given below. The compounds VI are reacted either with a compound $R^2$—Y, where Y represents a reactive leaving group such as chlorine, bromine, a sulfone, a sulfate, etc., or, in the case where $R^2$ represents a group of the formula C(A)—NH—$R^a$, with a compound $R^a$—N=C=A where $R^a$ and A are as defined in the general formula I. Compounds of the formula VII can be prepared by reacting 2-butyne-1,4-diol with $R^2$—Y in the presence of a base (e.g. an alkali metal hydroxide, an alkali metal alkoxide, sodium hydride, etc.) in a solvent such as DMSO, DMF, THF, pyridine, water, etc. (e.g. Tetrahedron Letters 38 (1997), 7887–7890; Bull. Chem. Soc. Jpn. 28 (1955), 80–82; J. Org. Chem. 18 (1953), 1601–1606). Compounds of the formula VII can also be prepared by reacting a suitably hydroxy-protected 1-chloro-4-hydroxy-2-butyne with an alkoxide, followed by cleavage of the protecting group as described in the literature (e.g. Bull. Chim. Soc. 1955, 502; J. Org. Chem. USSR (Engl. Transl.) 12 (1976), 505–507; J. Org. Chem. 63 (1998), 4291–4298).

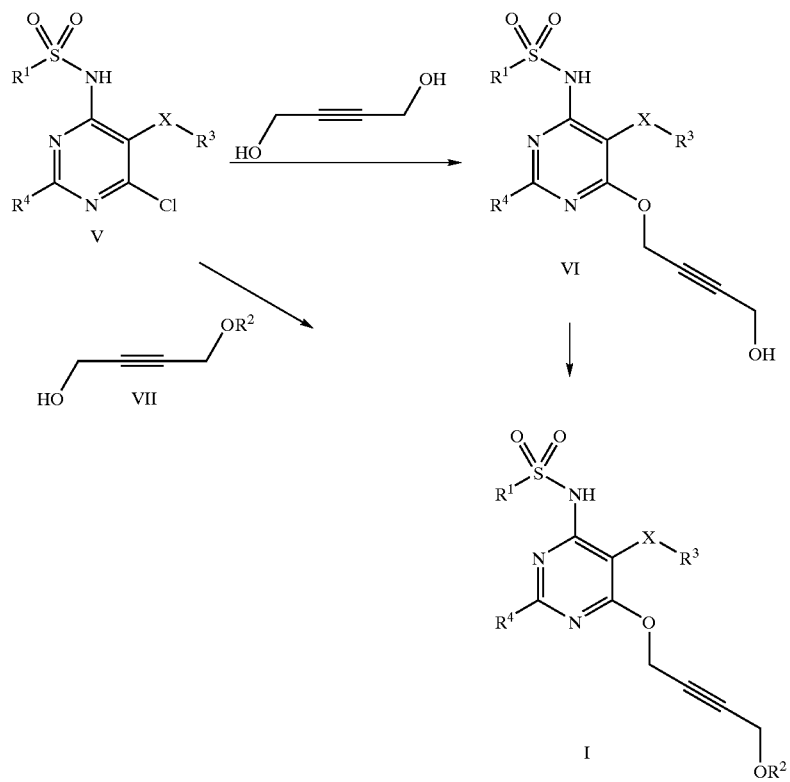

Compounds V are prepared from the corresponding dichloro compounds VIII (Bioorg. Med. Chem. Letters 7 (1997), 2223–2228, Chimia 50 (1996), 519–524, and references cited therein).

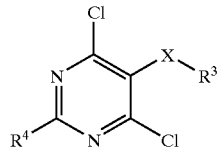

VIII

Treatment of VIII with an excess of the appropiate sulfonamide potassium salt in the presence or absence of a base (e.g. triethylamine, Hünig's base) in a solvent (e.g DMF, DMSO) at room temperature furnished the desired compounds V. The sulfonamide potassiums salts may be prepared according to e.g. Bioorg. Med. Chem. Letters 7 (1997), 2223–2228.

Compounds VIII could be prepared by treating the corresponding compounds IX (or tautomeric forms thereof) at elevated temperatures (30–120° C.) with a chlorinating agent such as $POCl_3$, $PCl_5$, or mixtures thereof, etc. each in the presence or absence of a base such as N,N-dialkylaniline or benzyltriethyl ammoniumchloride (e.g. Bioorg. Med. Chem. Lett., 7 (1997), 2223–2228; J. Med. Chem., 41 (1998), 3793–3803; J. Chem. Soc. 1959, 2214; Bull. Soc. Chim. Fr. 1959, 741–742).

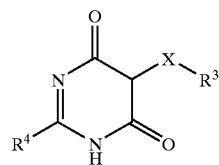

IX

In a standard method as described by Pinner (for review see e.g. The Pyrimidines, by D. J. Brown, Wiley Interscience, New York 1970), the compounds IX resulted from condensation of the corresponding amidines X (isolated as hydrochloride salts) with the appropriate malonic ester derivatives XI in the presence of a sodium alkoxide in a solvent such as methanol, ethanol, etc. at room temperature (e.g. Bull. Soc. Chim. Fr. 1960, 1648).

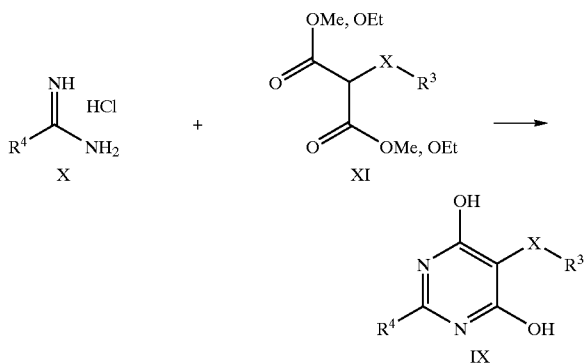

The amidines X were prepared form the corresponding nitrites XII by treatment of the nitriles XII either with sodium methylate in methanol followed by the addition of ammoniumchloride, or with lithium hexamethyldisilazan followed by the addition of hydrochloric acid in isopropanol (Advanced Organic Chemistry, by J. March, $3^{rd}$ edtion, Wiley 1985, p. 803 and references cited therein).

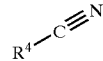

XII

The malonic ester derivatives XI were either commercially available or were prepared following the procedures found in the literature (e.g. J. Am. Chem. Soc. 62 (1940), 1154, 1155; ibid. 74 (1952), 4466; J. Chem. Soc. Perkin 1, 1979, 2382–2386; Collect. Czech. Chem. Comm. 55 (1990), 1278–1289; J. Med. Chem. Chim. Ther. 26 (1991), 599–604; Bull. Soc. Chim. Fr. 1973, 2065–2071).

As the case may be, compounds with one or more optically active carbon atom are resolved into pure enantiomers or diastereomers, mixtures of enantiomers or diastereomers, diastereomeric racemates, mixtures of diastereomeric racemates in a manner known per se, and, if desired, synthesised compounds of formula I were converted into a pharmaceutically acceptable salt in a manner known per se.

EXAMPLES

The following examples illustrate the invention. All temperatures are stated in ° C.

The compounds given below were prepared according to the procedure described above. All compounds were characterized by $^1$H-NMR (300 MHz) and occasionally by $^{13}$C-NMR (75 MHz) (Varian Oxford, 300 MHz; chemical shifts are given in ppm relative to the solvent used; multiplicities: s=singlet, d=doublet, t=triplet; m=multiplet), by LC-MS (Waters Micromass; ZMD-platform with ESI-probe with Alliance 2790 HT; Column: 2×30 mm, Gromsil ODS4, 3 μm, 120 Å; Gradient: 0–100% acetonitrile in water, 6 min, with 0.05% formic acid, flow: 0.45 ml/min; $t_r$ is given in min, molecular mass of the fraction at $t_r$), by TLC (TLC-plates from Merck, silica gel 60 $F_{254}$) and occasionally by melting point. Abbreviations: DCM=dichloromethane, MeOH=methanol, DMF=N,N-dimethylformamide, THF= tetrahydrofuran, DMSO=dimethyl sulfoxide, DMPU=1,3-dimethyl-3,4,5,6-tetrahydro-2(1H)-pyrimidinone, DMAP= 4-dimethylaminopyridine, DBU=1,8-diazabicyclo[5.4.0] undec-7-ene, min=minutes, h=hours.

Example 1 a) To a solution of 0.23 g sodium in 40 ml methanol was added 10.62 g 4-cyanopyridine at room temperature. Stirring was continued for 6 h followed by the addition of 5.9 g ammoniumchloride and stirring was continued for another 10 h. Then 120 ml diethylether was added and the precipitate was filtered off after 30 min and washed once with 20 ml of diethylether. The product was dried under high vacuum. 14.95 g 4-amidino-pyridine hydrochloride was obtained as a white powder.

b) 48 ml 2-methoxy-phenol (guajacol) were slowly added to a stirred suspension of 70.8 g potassium carbonate in 480 ml acetone followed by heating to 45° C. Then 63.2 ml dimethylchloromalonate in 50 ml acetone were added within 20 min. The reaction mixture was heated to reflux for 16 h. The solvent was evaporated under reduced pressure, the residue taken into water and extracted with DCM. The combined organic layers were dried over sodium sulfate and evaporated. The oily product was crystallized from methyl-tert.-butyl-ether. 86 g dimethyl-(o-methoxyphenoxy) malonate was obtained.

c) To a stirred solution of 9.7 g sodium methylate in 100 ml methanol a solution of 21.7 g dimethyl-(o-methoxyphenoxy)malonate in 50 ml methanol was added within 15 min and stirring was continued for 30 min followed by the addition of 15.0 g 4-amidino-pyridine hydrochloride followed by stirring at room temperature for 20 h. The reaction mixture was concentrated in vacuo. The solid residue was stirred with ether. The obtained powder was filtered off and dissolved in 300 ml water. Acetic acid was added to pH=4. The precipitated product was filtered off, washed with water and dried in vacuo at 50° C. 20.1 g 5-(o-methoxyphenoxy)-4,6-dihydroxy-2-(4-pyridyl)-pyrimidine (is possibly also present as the tautomeric 5-(o-methoxyphenoxy)-2-(4-pyridyl)-tetrahydropyrimidine-4,6-dion) was obtained as a white powder.

d) 10 g of the 5-(o-methoxyphenoxy)4,6-dihydroxy-2-(4-pyridyl)-pyrimidine, 11.2 g N-ethyldiisopropylamine, 11 g tetraethylammoniumchloride and 13.8 g phosphorous pentachloride were dissolved in 25 ml phosphorous oxychloride and heated to reflux for 3 h. The mixture was evaporated in vacuo, toluene was added and the mixture was again evaporated. The residue was taken into DCM and poured onto ice/water. The layers were separated, the organic layer was washed with water, dried over sodium sulfate and evaporated. After recrystallization from acetone, 6.52 g of 4,6-dichloro-5-(o-methoxyphenoxy)-2-(4-pyridyl)-pyrimidine was obtained.

e) 5-isopropyl pyridine-2-sulfonamide potassium salt was prepared according to procedures disclosed in EP 0713875 A1 and Bioorganic & Medicinal Chemistry Letters, 7 (1997), 2223–2228.

f) 1 g of 4,6-dichloro-5-(o-methoxyphenoxy)-2-(4-pyridyl)-pyrimidine and 1.43 g of 5-isopropyl pyridine-2-sulfonamide potassium salt were suspended in 20 ml of dry DMF. The mixture was stirred under argon at room temperature and became clear within a few h. After 16 h at room temperature, most of the solvent was removed by evaporation under reduced pressure. The residue was taken up in 20 ml water and the pH was adjusted to 4–5 by adding about 1 ml of acetic acid. A precipitate formed. The precipitate was filtered off, washed with water and dried. The yellow powder was further purified by column chromatography on silica gel eluting first with hexane:ethyl acetate 1:1 then with DCM-:MeOH 10:1. 1.43 g of 5-isopropyl-N-[6-chloro-5-(o-methoxyphenoxy)-2-(4-pyridyl)-4-pyrimidinyl]-2-pyridine sulfonamide was obtained as a slightly yellow powder. LC-MS: $t_R$=5.00 min, $[M+1]^+$=512.19, $[M-1]^-$=510.26.

g) At 0–5° C., 5.04 g of 2-butyne-1,4-diol was added portionwise to a stirred slurry of 0.7 g sodium hydride in 30 ml of dry DMF and 5 ml of DMPU. Stirring was continued until the evolution of gas had ceased. To the resulting suspension 1.5 g of 5-isopropyl-N-[6-chloro-5-(o-methoxyphenoxy)-2-(4-pyridyl)-4-pyrimidinyl]-2-pyridine sulfonamide was added at room temperature and the mixture was stirred at 95° C. for 24 h. Eventually, the slurry was allowed to cool to room temperature, was then poured onto 100 ml of an aqueous solution of 10% citric acid and extracted twice with 150 ml of ethyl acetate. The combined organic layers were washed twice with 50 ml of water, dried over MgSO$_4$ and evaporated. The remaining dark brown oil was purified by column chromatography on 80 g of silica gel eluting with DCM containing 0–5% of methanol. This gave 0.82 g of 5-isopropyl-N-[6-(4-hydroxy-2-butynyloxy)-5-(o-methoxyphenoxy)-2-(4-pyridyl)-4-pyrimidinyl]-2-pyridine sulfonamide as a pale yellow solid. LC-MS: $t_R$=4.39 min, $[M+1]^+$=562.29, $[M-1]^-$=560.41.

Example 2 a) A solution of 15.2 g of 4-tert.-butylbenzene sulfonyl chloride in 150 ml of THF was cooled with an ice bath. 15.2 ml of 25% aqueous ammonium hydroxide solution was added dropwise. After the addition was completed, the solution was stirred at room temperature for 15 min. The solvent was removed in vacuo. The residue was again dissolved in ethyl acetate and washed twice with water. The organic phase was dried over Na$_2$SO$_4$, evaporated and dried. The resulting 14.8 g of a white powder was dissolved in 75 ml of methanol and 7.5 g of potassium tert. butylate was added. The solution was briefly stirred at room temperature and evaporated. The resulting residue was carefully dried to give 16.3 g of 4-tert.-butylbenzene sulfonamide potassium salt as a white solid.

b) To a solution of 6.1 g of 4,6-dichloro-5-(o-methoxyphenoxy)-2-(4-pyridyl)-pyrimidine (Example 1, Section a) to d)) in 100 ml of dry DMF 8.8 g of 4-tert.-butyl benzene sulfonamide potassium salt was added at room temperature. The solution was stirred over night at room temperature. The solution was added to a mixture of 150 ml of water and 100 ml of diethyl ether. The pH was adjusted to 5 by adding acetic acid. The precipitate that formed was collected, washed with water and diethyl ether. The resulting powder was suspended in boiling ethyl acetate. The mixture was allowed to cool in an icebath. Eventually, the solid material was collected and dried to yield 6.6 g of 4-tert.-butyl-N-[6-chloro-5-(o-methoxyphenoxy)-2-(4-pyridyl)4-pyrimidinyl]-benzene sulfonamide as beige crystals. LC-MS: $t_R$=5.80 min, $[M+1]^+$=525.31, $[M-1]^-$=523.48.

c) At room temperature, 6.9 g of 2-butyne-1,4-diol was added portionwise to a stirred slurry of 0.96 g sodium hydride in 25 ml of dry DMF and 5 ml of dry DMPU. Stirring was continued until the evolution of gas had ceased. To the resulting suspension 2.1 g of 4-tert.-butyl-N-[6-chloro-5-(o-methoxyphenoxy)-2-(4-pyridyl)-4-pyrimidinyl]-benzene sulfonamide was added at room temperature and the mixture was stirred at 90° C. for 48 h. Eventually, the solvent was removed under reduced pressure and the resulting oil was treated with 150 ml of 10% aqueous acetic acid. The dark solution was extracted with 150 ml of DCM. The organic layer was washed with water, dried over MgSO$_4$ and evaporated. The resulting dark brown oil was further purified by column chromatography on silica gel eluting with toluene:ethyl acetate 4:1 to 1:4. This furnished 1.28 g of 4-tert.-butyl-N-[6-(4-hydroxy-2-butynyloxy)-5-(o-methoxyphenoxy)-2-(4-pyridyl)-4-pyrimidinyl]-benzene sulfonamide as a beige foam. LC-MS: $t_R$=4.87 min, $[M+1]^+$=575.32, $[M-1]^-$=573.45.

Example 3 a) To a suspension of 70 g of 2-bromo-5-methyl pyridine in 500 ml of water 200 ml 25% aqueous hydrochloric acid was added at room temperature. To the clear solution 68 g of thiourea was added and the mixture was heated to reflux. After 4 h another 34 g and after 18 h further 17 g of thiourea was added. After 24 h the solution was cooled with an icebath and 360 ml of 4 N sodium hydroxide solution was added. A precipitate formed which dissolved upon adding 600 ml of DCM. The organic layer was separated and washed with 500 ml of water. The aqueous phase was acidified to pH 3 using hydrochloric acid and repeatedly extracted with DCM. The combined organic layers were dried over MgSO$_4$, evaporated and dried under reduced pressure. This gave 46.9 g of a yellow solid which was recrystallised from boiling ethanol to furnish 37.6 g of 5-methyl-2-thio-pyridine in form of pale yellow platelets which sinter at 168° C. and gradually melt between 179 and 190° C. $^1$H-NMR(CDCl$_3$, 300 MHz): 2.17 (s, 3H); 7.24(dd, J=2.0, 8.8, 1H); 7.41(t, J=1.0, 1H); 7.47(d, J=8.8, 1H); 14.03(s br, 1H).

b) To a mixture of 100 ml of 25% aqueous hydrochloric acid and 250 ml of DCM was added 18 g of 5-methyl-2-thio-pyridine. While the mixture was vigorously stirred and kept at −10° C. 250 ml of an aqueous solution containing 13% of sodium hypochlorite was carefully added. Upon completion of the addition, stirring was continued for 10 min. The organic layer was separated. To the aqueous layer 250 ml of DCM was added and the mixture was again treated as before with a further 250 ml batch of bleach. Upon completion of the addition, the organic layer was separated. The aqueous layer was extracted five times with 200 ml DCM. The organic layers were combined, dried over $MgSO_4$ and evaporated. The resulting oil was dissolved in 125 ml of THF and cooled to −20° C. 25 ml of saturated aqueous ammonium hydroxide solution was slowly added. The mixture was stirred over night at room temperature. Excess of ammonia was neutralised by adding hydrochloric acid and the THF was removed in vacuo. The remaining aqueous solution was extracted three times with 150 ml of ethyl acetate. The combined organic layers were dried over $MgSO_4$ and the solvent was evaporated. The remaining solid was recrystallised from boiling ethyl acetate to yield 13.35 g of 5-methyl-2-pyridine sulfonamide in form of beige crystals. $^1$H-NMR($D_6$-DMSO, 300 MHz): 2.37(s, 3H); 7.36 (s, 2H); 7.78–7.85(m, 2H); 8.53(s, 1H); LC-MS: $t_R$=2.32 min, $[M+1]^+$=173.04, $[M-1]^-$=171.10.

c) To a solution of 18.54 g of 5-methyl-2-pyridine sulfonamide in 400 ml of methanol was added 12.08 g of potassium tert.-butylate. The solution was stirred at room temperature for 5 min. The solvent was removed under reduced pressure and the residue was dried under high vacuum to give 22.64 g of 5-methyl-2-pyridine sulfonamide potassium salt as a beige solid.

d) Under argon 4 g of 4,6-dichloro-5-(o-methoxyphenoxy)-2-(4-pyridyl)-pyrimidine (Example 1, section a) to d)) was dissolved in 40 ml of dry DMF and 3.62 g of 5-methylpyridine-2-sulfonamide potassium salt followed by 2.95 ml of Hünig's base was added. The dark solution was stirred at room temperature for 22 h. A further portion of 0.75 g of 5-methylpyridine-2-sulfonamide potassium salt was added and stirring was continued for 18 h. The reaction mixture was poured onto 150 ml of 10% citric acid in water and extracted four times with 150 ml of ethyl acetate. The combined organic phase was washed with water, dried over $MgSO_4$, and evaporated. The resulting residue was suspended in 20 ml of methanol and 20 ml of acetone. The precipitate was collected, washed with methanol:diethyl ether 1:1 and dried. This furnished 4.56 g of 5-methyl-N-[6-chloro-5-(o-methoxyphenoxy)-2-(4-pyridyl)4-pyrimidinyl]-2-pyridine sulfonamide as a beige powder. LC-MS: $t_R$=4.38 min, $[M+1]^+$=484.58, $[M-1]^-$=482.51.

e) At room temperature, 8.0 g of 2-butyne-1,4-diol was added portionwise to a stirred slurry of 0.99 g sodium hydride in 25 ml of dry DMF and 5 ml of dry DMPU. Stirring was continued until the evolution of gas had ceased. To the resulting suspension 2.0 g of 4-tert.-butyl-N-[6-chloro-5-(o-methoxyphenoxy)-2-(4-pyridyl)-4-pyrimidinyl]-benzene sulfonamide was added at room temperature and the mixture was stirred at 90° C. for 16 h. Eventually, the slurry was allowed to cool to room temperature, was then poured onto a mixture of 200 ml of an aqueous solution of 10% citric acid and 200 ml of ethyl acetate. A fine precipitate formed. The precipitate was filtered off, washed with water and ethyl acetate. The organic layer was separated and the aqueous layer was extracted two more times with ethyl acetate. The combined organic layers were dried over $MgSO_4$ and the solvent was removed to a volume of about 10 ml. The fine precipitate that formed was collected, washed with ethyl acetate, and combined with the precipitate isolated from the aqueous layer. This gave 1.65 g of 5-methyl-N-[6-(4-hydroxy-2-butynyloxy)-5-(o-methoxyphenoxy)-2-(4-pyridyl)-4-pyrimidinyl]-2-pyridine sulfonamide as a beige powder. LC-MS: $t_R$=3.81 min, $[M+1]^+$=534.63, $[M-1]^-$=532.54.

Example 4 a) 4,6-dihydroxy-5-(o-methoxyphenoxy)-2-(2-pyrimidinyl)-pyrimidine [or its tautomer 5-(o-methoxyphenoxy)-2-(2-pyrimidinyl)-tetrahydropyrimidine-4,6-dion] was prepared as disclosed in EP 0 526 708 A1 from 2-amidino-pyrimidine and dimethyl-(o-methoxyphenoxy)-malonate.

b) 4,6-dichloro-5-(o-methoxyphenoxy)-2-(2-pyrimidinyl)-pyrimidine was prepared as disclosed in EP 0 526 708 A1 from 4,6-dihydroxy-5-(o-methoxyphenoxy)-2-(2-pyrimidinyl)-pyrimidine (which may also be present in the tautomeric form 5-(o-methoxyphenoxy)-2-(2-pyrimidinyl)-tetrahydropyrimidine-4,6-dione).

c) A solution of 3.5 g of 4,6-dichloro-5-(o-methoxyphenoxy)-2-(2-pyrimidinyl)-pyrimidine and 4.98 g of 5-isopropyl-2-pyridine sulfonamide potassium salt (Example 1, section e) in 40 ml of DMSO was stirred at room temperature for 4 h. The mixture was poured onto water and extracted twice with diethyl ether. The aqueous layer was acidified with acetic acid. The precipitate that formed was collected, washed with water and diethyl ether and dried to furnish 5.1 g of 5-isopropyl-N-[6-chloro-5-(o-methoxyphenoxy)-2-(2-pyrimidinyl)-4-pyrimi-dinyl]-2-pyridine sulfonamide as a white solid. LC-MS: $t_R$=4.87 min, $[M+1]^+$=513.32, $[M-1]^-$=511.26.

d) 273 mg of 5-isopropyl-N-[6-(4-hydroxy-2-butynyloxy)-5-(o-methoxyphenoxy)-2-(2-pyrimidinyl)-4-pyrimidinyl]-2-pyridine sulfonamide was obtained as a beige foam starting from 600 mg of 5-isopropyl-N-[6-chloro-5-(o-methoxyphenoxy)-2-(2-pyrimidinyl)4-pyrimidinyl]-2-pyridine sulfonamide following the procedure given in Example 1g. LC-MS: $t_R$=4.31 min, $[M+1]^+$=563.71, $[M-1]^-$=561.59.

Example 5 a) 4-tert.-butyl-N-[6-chloro-5-(o-methoxyphenoxy)-2-(2-pyrimidinyl)-4-pyrimidinyl]benzene sulfonamide was prepared as disclosed in EP 0 526 708 A1 from 4,6-dichloro-5-(o-methoxyphenoxy)-2-(2-pyrimidinyl)-pyrimidine and p-tert.-butyl benzene sulfonamide potassium salt. LC-MS: $t_R$=5.50 min, $[M+1]^+$=526.29, $[M-1]^-$=524.43.

b) 295 mg of 4-tert.-butyl-N-[6-(4-hydroxy-2-butynyloxy)-5-(o-methoxyphenoxy)-2-(2-pyrimidinyl)4-pyrimidinyl]benzene sulfonamide was obtained as a beige foam starting from 1.4 g of 4-tert.-butyl-N-[6-chloro-5-(o-methoxyphenoxy)-2-(2-pyrimidinyl)-4-pyrimidinyl] benzene sulfonamide following the procedure given in Example 1g. LC-MS: $t_R$=5.06 min, $[M+1]^+$=576.33, $[M-1]^-$=574.45.

Example 6 a) To a suspension of 2.0 g of 4,6-dichloro-5-(o-methoxyphenoxy)-2-(2-pyrimidinyl)-pyrimidine (Example 4b) and 2.65 g of 5-methyl-2-pyridine sulfonamide potassium salt (Example 3c) in 40 ml of DMF was added 10 ml of DMSO. The mixture became clear and stirring was continued for 16 h at room temperature. Upon pouring the mixture onto 50 ml of 10% citric acid in water a white precipitate formed. The precipitate was collected, washed with water and ethyl acetate, and dried. This furnished 2.67 g of 5-methyl-N-[6-chloro-5-(o-methoxyphenoxy)-2-(2-pyrimidinyl)-4-pyrimidinyl]-2-pyridine sulfonamide as a white powder. LC-MS: $t_R$=4.23 min, [M+1]$^+$=485.56, [M−1]$^−$=483.48.

b) 347 mg of 5-methyl-N-[6-(4-hydroxy-2-butynyloxy)-5-(o-methoxyphenoxy)-2-(2-pyrimidinyl)-4-pyrimidinyl]-2-pyridine sulfonamide was obtained as a pale yellow foam starting from 1 g of 5-methyl-N-[6-chloro-5-(o-methoxyphenoxy)-2-(2-pyrimidinyl)-4-pyrimidinyl]-2-pyridine sulfonamide following the procedure given in Example 1g. LC-MS: $t_R$=3.90 min, [M+1]$^+$=535.66, [M−1]$^−$=533.55.

Example 7 a) A solution of 10 g of dimethyl-(o-methoxyphenoxy) malonate (Example 1b) in 80 ml dry methanol was cooled to 0° C. 6.71 g of sodium methylate was added portionenwise. To the suspension was added 2.84 g of acetamidine hydrochloride and the mixture was stirred overnight at room temperature. The solvent was removed under reduced pressure and the residue was suspended in 100 ml of diethyl ether. The solid was filtered off, washed with another portion of 100 ml of diethyl ether and dissolved in 50 ml of water. The pH was adjusted to 4 by adding 25 ml of glacial acetic acid. The white precipitate that formed was filtered off, washed with water and dried to yield 5.17 g of 5-(o-methoxyphenoxy)-4,6-dihydroxy-2-methyl-pyrimidine (or a tautomer) as a white powder.

b) A solution of 10.9 g of 5-(o-methoxyphenoxy)-4,6-dihydroxy-2-methyl-pyrimidine (or a tautomer) in 150 ml of POCl$_3$ was stirred at 50° C. for 72 h. The excess of POCl$_3$ was evaporated, toluene was added to coevaporate traces of POCl$_3$. Eventually, an ice:water mixture was carefully added to the residue and the pH was adjusted to 8 using 3 N sodium hydroxide solution. The mixture was further diluted with 300 ml of water and extracted with 500 ml of DCM. The organic layer was separated, washed with 300 ml of water, dried over Na$_2$SO$_4$ and evaporated. The residue was dissolved again in DCM and filtered through a pad of silica gel eluting with DCM. The solvent was removed in vacuo. The resulting residue was dried to furnish 8.7 g of 4,6-dichloro-5-(o-methoxyphenoxy)-2-methyl-pyrimidine as a beige powder.

c) To a solution of 2.15 g of 4,6-dichloro-5-(o-methoxyphenoxy)-2-methyl-pyrimidine in 40 ml of DMSO was added 3.59 g of 5-isopropyl-2-pyridine sulfonamide potassium salt. The mixture was stirred for 72 h at room temperature. The solution was diluted with 350 ml of water and extracted twice with 200 ml of diehtyl ether. The organic layers were extracted twice with water. The combined aqueous layers were acidified to pH 4 with 5 ml of acetic acid and extracted twice with DCM. The organic layers were washed with water, and dried over Na$_2$SO$_4$. The solution was treated with activated charcoal, filtered over Celite and evaporated. The residue was suspended in 30 ml of diethyl ether, filtered off and dried to give 3.15 g of 5-isopropyl-N-[6-chloro-5-(o-methoxyphenoxy)-2-methyl-4-pyrimidinyl]-2-pyridine sulfonamide as a pale beige powder. LC-MS: $t_R$=5.18 min, [M+1]$^+$=449.25, [M−1]$^−$=447.31.

d) 440 mg of 5-isopropyl-N-[6-(4-hydroxy-2-butynyloxy)-5-(o-methoxyphenoxy)-2-methyl-4-pyrimidinyl]-2-pyridine sulfonamide was obtained as a beige foam starting from 600 mg of 5-isopropyl-N-[6-chloro-5-(o-methoxyphenoxy)-2-methyl-4-pyrimidinyl]-2-pyridine sulfonamide following the procedure given in Example 1g, but stirring the reaction mixture for 48 h at 95° C. LC-MS: $t_R$=4.74 min, [M+1]$^+$=499.25, [M−1]$^−$=497.33.

Example 8 a) At room temperature 2.95 g of 5-methyl-2-pyridine sulfonamide potassium salt (Example 3c) was added to a suspension of 2 g of 4,6-dichloro-5-(o-methoxyphenoxy)-2-methyl-pyrimidine (Example 7b) in 30 ml DMSO. The mixture was stirred at room temperature for 48 h and was then poured onto 300 ml of water. The aqueous solution was extracted twice with 200 ml of diethyl ether. The organic layers were extracted with water and the aqueous layers were combined and acidified with 3 ml of acetic acid to pH 4. Precipitation of the product was enhanced by adding 100 ml of saturated aqueous sodium chloride and cooling the mixture to 0° C. Eventually, the precipitate was filtered off, washed with cold water and dried under high vacuum to give 2.26 g of 5-methyl-N-[6-chloro-5-(o-methoxyphenoxy)-2-methyl-4-pyrimidinyl]-2-pyridine sulfonamide as a beige powder. LC-MS: $t_R$=4.79 min, [M+1]$^+$=421.42, [M−1]$^−$=419.46.

b) 584 mg of 5-methyl-N-[6-(4-hydroxy-2-butynyloxy)-5-(o-methoxyphenoxy)-2-methyl-4-pyrimidinyl]-2-pyirdine sulfonamide was obtained as a beige powder starting from 950 mg of 5-methyl-N-[6-chloro-5-(o-methoxyphenoxy)-2-methyl4-pyrimidinyl]-2-pyridine sulfonamide following the procedure given in Example 1g, but stirring the reaction mixture for 72 h at 95° C. LC-MS: $t_R$=4.32 min, [M+1]$^+$=471.57, [M−1]$^−$=469.40.

Example 9 a) A solution of 32.75 g of dimethyl-(o-methoxyphenoxy) malonate (Example 1 b) in 250 ml of methanol was cooled to 0° C. 20.0 g sodium methylate was added portionwise and upon completion of the addition the mixture was stirred at room temperature for 6 h. Then 25.0 g of morpholinoformamidine hydrobromide was added and stirring was continued for 72 h. The solvent of the beige suspension was evaporated and the residue was washed twice with 150 ml of diethyl ether. The remaining powder was dissolved in 200 ml of water. Upon adjusting the pH to 4 with 50 ml of acetic acid a precipitate formed. The precipitate was collected, washed with water and dried under high vacuum to yield 17.01 g of 5-(o-methoxyphenoxy)-4,6-dihydroxy-2-(N-morpholino)-pyrimidine (or a tautomer) as a slightly beige powder.

b) At 0° C. 50 ml of POCl$_3$ was carefully added to 27.5 ml of Hünig's base. To this mixture 17 g of 5-(o-methoxyphenoxy)-4,6-dihydroxy-2-(N-morpholino)-pyrimidine was added portionwise. The resulting mixture was stirred over night at 130° C. The excess of reagents was evaporated and traces of POCl$_3$ were removed by coevaporation with toluene. The black residue was treated with 50 ml of DCM and 50 ml of a water:ice mixture. After stirring for 15 min, the mixture was diluted with 400 ml of water and 400 ml of DCM. The organic layer was separated and washed with 300 ml of water. The aqueous layer was extracted with 400 ml of DCM. The combined DCM layers were dried over Na$_2$SO$_4$ and the solvend was removed to a volume of about 100 ml. The remaining solution was filtered over 50 g of silica gel eluting with DCM. The filtrate was evaporated. The resulting residue was suspended in 50 ml of diethyl ether. The solid was filtered off and dried to give 13.85 g of 4,6-dichloro-5-(o-methoxyphenoxy)-2-(N-morpholino)-pyrimidine as a white crystalline powder.

c) To a suspension of 4 g of 4,6-dichloro-5-(o-methoxyphenoxy)-2-(N-morpholino)-pyrimidine in 60 ml of DMSO was added 5.32 g of 5-isopropyl-2-pyridine sulfonamide potassium salt (Example 3c) and 0.98 ml of Hünig's base. The mixture was stirred at 65° C. for 72 h. The dark solution was poured onto 500 ml of water and quickly filtered through celite. The filtrate was extracted with 500 ml and 250 ml of diethyl ether. The organic layers were extracted with 100 ml of water. The aqueous layers were combined, acidified with 3.5 ml of acetic acid and cooled to 0° C. The precipitate that formed was collected, washed with cold water and dried under high vacuum to furnish 4.94 g of 5-isopropyl-N-[6-chloro-5-(o-methoxyphenoxy)-2-(N-morpholino)-4-pyrimidinyl]-2-pyridine sulfonamide as a brownish powder. LC-MS: $t_R$=5.46 min, $[M+1]^+$=520.22, $[M-1]^-$=518.36.

d) At 0–5° C. 3.97 g of 2-butyne-1,4-diol was added portionwise to a stirred slurry of 0.55 g sodium hydride in 30 ml of dry DMF and 7 ml of DMPU. Stirring was continued until the evolution of gas had ceased. To the resulting suspension 1.2 g of 5-isopropyl-N-[6-chloro-5-(o-methoxyphenoxy)-2-(N-morpholino)-4-pyrimidinyl]-2-pyridine sulfonamide was added at room temperature and the mixture was stirred at 95° C. for 6 days. Eventually, the slurry was allowed to cool to room temperature, was then poured onto 100 ml of an aqueous solution of 10% citric acid and extracted twice with 150 ml of ethyl acetate. The combined organic layers were washed twice with 75 ml of water, dried over $MgSO_4$ and evaporated. The remaining brown oil was purified by column chromatography on 120 g of silica gel eluting with DCM containing 0–2% of methanol. Fractions containing the desired compound were combined, evaporated and the residue was further purified by recrystallisation from diethyl ether: hexane. This gave 327 mg of 5-isopropyl-N-[6-(4-hydroxy-2-butynyloxy)-5-(o-methoxyphenoxy)-2-(N-morpholino)-4-pyrimidinyl]-2-pyridine sulfonamide as colourless crystals with a melting point of 196.0–197.5° C. LC-MS: $t_R$=4.89 min, $[M+1]^+$=570.30, $[M-1]^-$=568.43. Furthermore, 494 mg of the starting material was recovered as a beige foam.

Example 10 a) At 5° C. 12.7 g of sodium methylate was added portionwise to a solution of 18.9 g of dimethyl-(o-methoxyphenoxy)malonate (Example 1b) in 450 ml of methanol. Upon completion of the addition stirring was continued at room temperature for 30 min followed by the addition of 6 g of formamidine hydrochloride. The mixture was stirred at room temperature for 72 h. Eventually, the solvent was removed under reduced pressure and the remaining residue was suspended in diethyl ether. The solid material was filtered off and dissolved in 100 ml of water. The solution was acidified with conc. hydrochloric acid. A white precipitate formed. The precipitate was collected, washed with water and dried to give 15.1 g of 5-(o-methoxyphenoxy)-4,6-dihydroxy-pyrimidine (or a tautomer) as a white powder.

b) To a solution of 7.5 g of 5-(o-methoxyphenoxy)-4,6-dihydroxy-pyrimidine in 90 ml of $POCl_3$ 24 ml of N,N-dimethylaniline was added. The mixture was heated to 160° C. and stirred for 2.5 h. Excess of $POCl_3$ was distilled off under reduced pressure. Traces of $POCl_3$ were coevaporated with toluene. The remaining oil was treated with a water:ice mixture. The mixture was acidified with 1 N hydrochloric acid and extracted twice with diethyl ether. The combined organic layers were washed twice with dilute aqueous hydrochloric acid, dried over $MgSO_4$ and evaporated. The remaining solid was washed with methanol and dried. This gave 4.75 g of 4,6-dichloro-5-(o-methoxyphenoxy)-pyrimidine as a pale yellow powder.

c) To a solution of 2 g of 4,6-dichloro-5-(o-methoxyphenoxy)-pyrimidine in 40 ml of DMSO 3.7 g of 4-tert.butylbenzene sulfonamide potassium salt was added. The resulting solution was stirred for 20 h at room temperature. Eventually, the mixture was poured onto 400 ml of water and washed twice with 200 ml of diethyl ether. The organic layers were extracted with 200 ml of water. The combinded aqueous layers were acidified with conc. hydrochloric acid. The mixture was cooled to 0° C. and 100 ml of brine was added. The precipitate that formed was collected and dried to yield 2.7 g of 4-tert.-butyl-N-[6-chloro-5-(o-methoxyphenoxy)-4-pyrimidinyl]-benzene sulfonamide as a white powder. LC-MS: $t_R$=5.80 min, $[M+1]^+$=448.17, $[M-1]^-$=446.21.

d) To a slurry of 0.79 g of sodium hydride in 45 ml of DMF and 15 ml of DMPU 5.68 g of 2-butyne-1,4-diol was added at 10° C. The mixture was stirred until no more gas evolved. Then 1.48 g of 4-tert.-butyl-N-[6-chloro-5-(o-methoxyphenoxy)-4-pyrimidinyl]-benzene sulfonamide was added and the mixture was stirred at 90° C. for 72 h. The solvent was removed in vacuo and the residue was taken up in 150 ml of 10% aqueous acetic acid. The mixture was extracted three times with 150 ml of ethyl acetate. The combined organic layers were washed with water and brine, dried over $MgSO_4$ and evaporated. The resulting brown oil was purified by column chromatography on silica gel eluting with hexane:ethyl acetate 3:1 to 1:1. This furnished 320 mg of 4-tert.-butyl-N-[6-(4-hydroxy-2-butynyloxy)-5-(o-methoxyphenoxy)-4-pyrimidinyl]-benzene sulfonamide as a slightly brown foam. LC-MS: $t_R$=5.21 min, $[M+1]^+$=498.35, $[M-1]^-$=496.49.

Example 11 a) A solution of 6.8 g of sodium methylate in 200 ml of methanol was cooled to 0° C. A solution of 10.3 g of diethyl 2-(p-tolyl)-malonate in 50 ml of methanol was slowly added. Upon completion of the addition the solution was allowed to come to room temperature and 7.57 g of 4-amidino-pyridine hydrochloride (Example 1a) was added. The mixture was stirred at room temperature for 16 h. Eventually, the solvent was removed under reduced pressure and the remaining residue was dissolved in 2 M hydrochloric acid. The solution was extracted with diethyl ether, then adjusted to pH 5 with 10 M sodium hydroxide solution. A precipitate formed. The precipitate was collected, washed with cold water and dried at 60° C. under high vacuum. This gave 8.77 g of 4,6-dihydroxy-2-(4-pyridyl)-5-(p-tolyl)-pyrimidine (or a tautomer) as orange crystals.

b) To a mixture of 8.0 g of 5-(p-tolyl)-4,6-dihydroxy-pyrimidine and 100 ml of $POCl_3$ 25 ml of diethylamine was added at room temperature. The mixture was stirred for 16 h at 60° C. The excess of $POCl_3$ was distilled off under reduced pressure. The remaining oil was dissolved in 300 ml of DCM and treated with 300 ml of water. The aqueous layer was separated and extracted three times with DCM. The combined organic layers were washed with water and brine, dried over $MgSO_4$ and evaporated. The resulting residue was suspended in isopropanol. The solid material was collected, washed with isopropanol, and diethyl ether and dried to give 7.2 g of 4,6-dichloro-2-(4-pyridyl)-5-(p-tolyl)-pyrimidine as a white crystalline powder.

c) A mixture of 654 mg of 4,6-dichloro-2-(4-pyridyl)-5-(p-tolyl)-pyrimidine and 1051 mg of 5-isopropyl-2-pyridine sulfonamide potassium salt (Example 1e) in 20 ml of DMF was stirred for 16 h at room temperature. Eventually, the solvent was distilled off under reduced pressure and the resulting residue was treated with 100 ml of 10% aqueous acetic acid and 100 ml of DCM. The layers were separated. The aqueous layer was extracted two more times with DCM. The combined organic layers were washed once with water, dried over $MgSO_4$ and evaporated. The remaining residue was crystallised from isopropanol:diethyl ether. The yellow crystals were collected, washed with cold isopropanol and diethyl ether, and dried under high vacuum to furnish 870 mg of 5-isopropyl-N-[6-chloro-5-(p-tolyl)-2-(4-pyridyl)4-pyrimidinyl]-2-pyridine sulfonamide. LC-MS: $t_R$=5.06 min, $[M+1]^+$=480.40, $[M-1]^-$=478.48.

d) To a slurry of 0.34 g of sodium hydride in 15 ml of DMF and 4 ml of DMPU 2.4 g of 2-butyne-1,4-diol was added at room temperature. The mixture was stirred until no more gas evolved. Then 0.67 g of 5-isopropyl-N-[6-chloro-5-(p-tolyl)-2-(4-pyridyl)-4-pyrimidinyl]-2-pyridine sulfonamide was added and the mixture was stirred at 90° C. for 48 h. The solvent was removed in vacuo and the residue was taken up in 100 ml of 10% aqueous acetic acid. The mixture was extracted three times with 100 ml of ethyl acetate. The combined organic layers were washed with water and brine, dried over $MgSO_4$ and evaporated. The resulting brown oil was purified by column chromatography on silica gel eluting with DCM containing 4–10% of methanol. This furnished a fraction which after recrystallisation from DCM: ethyl acetate gave 43 mg of 5-isopropyl-N-[6-(4-hydroxy-2-butynyloxy)-5-(p-tolyl)-2-(4-pyridyl)-4-pyrimidinyl]-2-pyridine sulfonamide as pale yellow crystals. A second fraction gave 456 mg of 5-isopropyl-N-[6-(4-hydroxy-2-butynyloxy)-5-(p-tolyl)-2-(4-pyridyl)-4-pyrimidinyl]-2-pyridine sulfonamide with about 90% purity as a brown oil. LC-MS: $t_R$=4.53 min, $[M+1]^+$=530.23, $[M-1]^-$=528.21.

Example 12 a) At 0° C. a solution of 14.2 g of diethyl 2-(p-tolyl)-malonate in 50 ml of methanol was slowly added to a solution of 9.4 g of sodium methylate in 300 ml of methanol. Upon completion of the addition the reaction mixture was allowed to warm up and 5.4 g of formamidine hydrochloride was added. The mixture was stirred at room temperature for 16 h. The solvent was removed under reduced pressure and the remaining residue was treated with 150 ml of 2 N hydrochloric acid. The suspension was stirred for 0.5 h. At 0–5° C., the pH was carefully adjusted to 4 using 10 N sodium hydroxide solution. The precipitate was collected, washed with cold water, isopropanol, and diethyl ether and dried under high vacuum at 65° C. to give 11.2 g of 4,6-dihydroxy-5-(p-tolyl)-pyrimidine (or a tautomer) as a white powder.

b) At room temperature 10 ml of N,N-dimethylaniline was added to a mixture of 5.1 g of 4,6-dihydroxy-5-(p-tolyl)-pyrimidine and 75 ml of $POCl_3$. The reaction mixture was stirred at 70° C. for 16 h. The excess of $POCl_3$ was distilled off and the remaining oil was treated with a ice-:water mixture and extracted three times with diethyl ether. The combined organic layers were washed with 1N aqueous hydrochloric acid followed by brine, dried over $MgSO_4$ and evaporated. The remaining brown oil was crystallised from isopropanol. The pale yellow crystals were collected, washed with cold isopropanol and dried under high vacuum to furnish 4.1 g of 4,6-dichloro-5-(p-tolyl)-pyrimidine.

c) A mixture of 0.8 g of 4,6-dichloro-5-(p-tolyl)-pyrimidine and 1.68 g of 4-tert.-butylbenzene sulfonamide potassium salt (Example 2a) in 20 ml of DMSO was stirred at room temperature for 24 h. The mixture was poured onto 200 ml of water and extracted twice with 100 ml of diethyl ether. The organic layers were extracted twice with 50 ml of water. The combined aqueous layers were acidified hydrochloric acid. The resulting fine suspension was extracted twice with ethyl acetate. The combined organic layers were dried over $Na_2SO_4$ and evaporated. The residue was dried under high vacuum to give 1.34 g 4-tert.-butyl-N-[6-chloro-5-(p-tolyl)-4-pyrimidinyl]-benzene sulfonamide as a white powder. LC-MS: $t_R$=5.92 min, $[M+1]^+$=416.20, $[M-1]^-$=414.24.

d) 700 mg of 4-tert.-butyl-N-[6-(4-hydroxy-2-butynyloxy)-5-(p-tolyl)-4-pyrimidinyl]-benzene sulfonamide was obtained as a brown glass starting from 1.45 g of 4-tert.-butyl-N-[6-chloro-5-(p-tolyl)-4-pyrimidinyl]-benzene sulfonamide following the procedure given in Example 10d. LC-MS: $t_R$=5.38 min, $[M+1]^+$=466.24, $[M-1]^-$=464.32.

Example 13 a) A solution of 2.71 g of 4,6-dichloro-5-(o-methoxyphenoxy)-pyrimidine (Example 10b) and 5.0 g of 5-isopropyl pyridine-2-sulfonamide potassium salt (Example 1e) in 50 ml of DMF was stirred at room temperature for 20 h. The solvent was removed in vacuo, the residue was taken up in 200 ml of 10% aqueous acetic acid and extracted three times with ethyl acetate. The combined organic layers were washed with water and brine, dried over $MgSO_4$ and evaporated. The crude product was crysallised from a mixture of 2-propanol and diethyl ether. The crystals were collected, washed with cold 2-propanol and diethyl ether and dried to give 2.8 g of 5-isopropyl-N-[6-chloro-5-(o-methoxyphenoxy)-4-pyrimidinyl]-2-pyridine sulfonamide as white crystals. LC-MS: $t_R$=4.99 min, $[M+1]^+$=435.25, $[M-1]^-$=433.28.

b) To a solution of 11.02 g of 2-butyne-1,4-diol in 100 ml of DMF and 30 ml of DMPU was added 2.8 g sodium hydride in portions. After completion of the addition stirring was continued for 1.5 h followed by the addition of 2.78 g of 5-isopropyl-N-[6-chloro-5-(o-methoxyphenoxy)-4-pyrimidinyl]-2-pyridine sulfonamide. The mixture was heated to 90° C. and stirred for 65 h. The solvent was removed in vacuo, the residue was taken up in 250 ml of 10% aqueous citric acid and extracted twice with 250 ml of ethyl acetate. The organic phase was washed with water and brine, dried over $MgSO_4$ and evaporated. Column chromatography of the crude product on silica gel eluting with hexane:ethyl acetate 1:1 to 1:4 furnished 1.27 g of 5-isopropyl-N-[6-(4-hydroxy-2-butynyloxy)-5-(o-methoxyphenoxy)$_4$-pyrimidinyl]-2-pyridine sulfonamide as a brown solid. Beige crystals were obtained for analytical purposes after crystallisation of a part of the isolated product from 2-propanol. LC-MS: $t_R$=4.50 min, $[M+1]^+$=485.27, $[M-1]^-$=483.41.

Example 14 a) A solution of 15.2 g of 4-tert.-butylbenzene sulfonyl chloride in 150 ml of THF was cooled with an ice bath. 15.2 ml of 25% aqueous ammonium hydroxide solution was added dropwise. After the addition was completed, the solution was stirred at r.t. for 15 min. The solvent was removed in vacuo. The residue was again dissolved in ethyl acetate and washed twice with water. The organic phase was dried over $Na_2SO_4$, evaporated and dried. The resulting 14.8 g of a white powder was dissolved in 75 ml of methanol and 7.5 g of potassium tert. butylate was added. The solution was briefly stirred at r.t. and evaporated. The resulting residue was carefully dried to give 16.3 g of 4-tert.-butylbenzene sulfonamide potassium salt as a white solid.

b) A solution of 2.0 g of 4,6-dichloro-5-(2-methoxyphenoxy)-2-(N-morpholino)-pyrimidine (Example 9b) and 2.96 g of 4-tert.-butylbenzene sulfonamide potassium salt in 30 ml of DMSO was stirred at r.t. for 24 h. After 1 g of 4-tert.-butylbenzene sulfonamide potassium salt had been added, stirring was continued for another 24 h at r.t. followed by 16 h at 55° C. Eventually, the mixture was poured into 350 ml of water and 350 ml of ether. The mixture was acidified by adding acetic acid. A white, sticky precipitate formed. The mixture was stirred at 0° C. for 1 h. The precipitate was filtered off, washed with water and ether and dissolved again in ethyl acetate. The solvent was removed in vacuo and the remaining solid was suspended in 100 ml of diethyl ether. The solid was filtered off, washed with additional diethyl ether and dried to give 2.57 g of 4-tert.-butyl-N-[6-chloro-5-(2-methoxy-phenoxy)-2-morpholin-4-yl-pyrimidin-4-yl]-benzene sulfonamide as a white powder. LC-MS: $t_R$=5.98 min, $[M+1]^+$=533.29, $[M-1]^-$=531.41.

c) To a suspension of 675 mg of NaH in 45 ml of DMF and 5 ml of DMPU was added 4.85 g of 2-butyne-1,4-diol. The mixture was stirred at room temperature until evolution of gas had ceased. Then 1.5 g of 4-tert.-butyl-N-[6-chloro-5-(2-methoxy-phenoxy)-2-morpholin-4-yl-pyrimidin-4-yl]-benzene sulfonamide was added and the resulting mixture was heated to 95° C. and stirred for 5 days. Eventually, the mixture was pourred into 150 ml of 10% aqueous citric acid and extracted three times with 150 ml of ethyl acetate. The organic layers were washed with water and brine, dried over MgSO$_4$ and evaporated. The resulting residue was purified by column chromatography on silicagel eluting with hexane:ethyl acetate 1:1 to give 265 mg of 4-tert.-butyl-N-[6-(4-hydroxy-2-butynyloxy)-5-(2-methoxy-phenoxy)-2-morpholin-4-yl-pyrimidin-4-yl]-benzene sulfonamide as a beige foam along with 1.13 g of the starting material 4-tert.-butyl-N-[6-chloro-5-(2-methoxy-phenoxy)-2-morpholin-4-yl-pyrimidin-4-yl]-benzene sulfonamide. LC-MS: $t_R$=5.39 min, $[M+1]^+$=583.41, $[M-1]^-$=581.35.

Example 15 a) To a suspension of 4 g of 4,6-dichloro-5-(2-methoxyphenoxy)-2-(N-morpholino)-pyrimidine (Example 9b) in 20 ml of DMSO was added 4.72 g of 5-methyl-2-pyridine sulfonamide potassium salt (Example 3c). The mixture was stirred at 55° C. for 17 h. The dark solution was poured into 500 ml of water and quickly filtered through celite. The filtrate was extracted with 500 ml and 250 ml of diethyl ether. The organic layers were extracted with 100 ml of water. The aqueous layers were combined, acidified with 3.5 ml of acetic acid and cooled to 0° C. The precipitate that formed was collected, washed with cold water and dried under high vacuum to furnish 4.42 g of 5-methyl-N-[6-chloro-5-(2-methoxyphenoxy)-2-(N-morpholino)-4-pyrimidinyl]-2-pyridine sulfonamide as a brownish powder. LC-MS: $t_R$=4.80 min, $[M+1]^+$=492.31, $[M-1]^-$=490.37.

b) To a suspension of 712 mg of NaH in 30 ml of DMF and 7 ml of DMPU was added 5.11 g of 2-butyne-1,4-diol. The mixture was stirred at room temperature until evolution of gas had ceased. Then 1.45 g of 5-methyl-N-[6-chloro-5-(2-methoxyphenoxy)-2-(N-morpholino)-4-pyrimidinyl]-2-pyridine sulfonamide was added and the resulting mixture was heated to 95° C. and stirred for 4 days. Eventually, the mixture was pourred into 200 ml of 10% aqueous citric acid and extracted three times with 200 ml of ethyl acetate. The organic layers were washed with water and brine, dried over MgSO$_4$ and evaporated. The resulting residue was purified by column chromatography on silicagel eluting with a gradient of hexane:ethyl acetate 1:1 to ethyl acetate to give 470 mg of 5-methyl-N-[6-(4-hydroxy-2-butynyloxy)-5-(2-methoxyphenoxy)-2-(N-morpholino)-4-pyrimidinyl]-2-pyridine sulfonamide as a beige powder along with 660 mg g of the starting material 5-methyl-N-[6-chloro-5-(2-methoxyphenoxy)-2-(N-morpholino)-4-pyrimidinyl]-2-pyridine sulfonamide. LC-MS: $t_R$=4.33 min, $[M+1]^+$=542.35, $[M-1]^-$=540.32.

Example 16 a) A mixture of 10 g of 4,6-dichloro-5-(p-tolyl)-pyrimidine (Example 12b) and 0.8 g of 5-isopropyl pyridine-2-sulfonamide potassium salt (Example 1e) in 100 ml of DMF was stirred at room temperature for 72 h. The solvent was partially removed in vacuo before the mixture was treated with 50 ml of diethyl ether. Under vigorous stirring, the pH of the aqueous phase was adjusted to 3 by adding a 10% aqueous citric acid solution. Stirring was continued for 15 min at 10° C. The precipitate that formed was collected, washed with water and diethtyl ether and dried under high vaccum at 50° C. This furnished 7.67 g of 5-isopropyl-N-[6-chloro-5-(p-tolyl)-4-pyrimidinyl]-2-pyridine sulfonamide as a white powder. LC-MS: $t_R$=5.13 min, $[M+1]^+$=403.24, $[M-1]^-$=401.28.

b) To a solution of 21.5 g of 2-butyne-1,4-diol in 200 ml of DMF and 50 ml of DMPU was added in portions 5.5 g of NaH 55% in mineral oil. After the evolution of gas had ceased 5.04 g of 5-isopropyl-N-[6-chloro-5-(p-tolyl)-4-pyrimidinyl]-2-pyridine sulfonamide was added and the resulting mixture was stirred for 80 h at 90° C. The solvent was removed in vacuo and the residue was partitioned between 300 ml of 10% aqueous citric acid and 300 ml of ethyl acetate. The aqueous phase was extracte two more times with ethyl acetate. The combined organic layers were washed with water and brine, dried over MgSO$_4$ and evaporated. The crude product was purified by column chromatography on silica gel eluting with hexane:ethyl acetate from 1:1 to 1:4 to give 2.0 g of 5-isopropyl-N-[6-(4-hydroxy-2-butynyloxy)-5-(p-tolyl)-4-pyrimidinyl]-2-pyridine sulfonamide as a brown solid. LC-MS: $t_R$=4.64 min, $[M+1]^+$=453.28, $[M-1]^-$=451.40.

Example 17

To a suspension of 14 mg of a 55% sodium hydride dispersion in mineral oil in 2 ml of dry DMF and 2 ml of dry THF 80 mg of 5-isopropyl-N-[6-(4-hydroxy-2-butynyloxy)-5-(o-methoxyphenoxy)-2-(4-pyridyl)-4-pyrimidinyl]-2-pyridine sul-fonamide (Example 1g) was added. After stirring for 10 min, 41 mg of 2-chloro-pyrimidine was added. Stirring was continued for 1 h at 70° C. The reaction mixture was poured onto 50 ml of 10% aqueous citric acid. The solution was extracted twice with 50 ml of ethyl acetate. The combined organic layers were twice washed with water, dried over MgSO$_4$ and evaporated. The remaining residue was purified by column chromagraphy on silica gel eluting with a gradient of 0–2% of methanol in DCM. This furnished 72 mg of 5-isopropyl-N-[6-(4-(2-pyrimidinyloxy)-2-butynyloxy)-5-(o-methoxy-phenoxy)-2-(4-pyridyl)-4-pyrimidinyl]-2-pyridine sulfonamide as a colourless foam. LC-MS: $t_R$=4.74 min, $[M+1]^+$=640.35, $[M-1]^-$=638.49.

Example 18

88 mg of 5-isopropyl-N-[6-(4-(4,6-dimethoxy-2-pyrimidinyloxy)-2-butynyloxy)-5-(o-methoxyphenoxy)-2-

(4-pyridyl)-4-pyrimidinyl]-2-pyridine sulfonamide was obtained as a pale yellow solid starting from 80 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 78 mg of 4,6-dimethoxy-2-methyl-sulfonylpyrimidine following the procedure given in Example 17. LC-MS: $t_R$=5.34 min, [M+1]$^+$=700.42, [M−1]$^-$=698.52.

Example 19

To a suspension of 76 mg of a 55% sodium hydride dispersion in mineral oil in 15 ml of dry THF 403 mg of 4-tert.-butyl-N-[6-(4-hydroxy-2-butynyloxy)-5-(o-methoxyphenoxy)-2-(4-pyridyl)4-pyrimidinyl]-benzene sulfonamide (Example 2c) was added. After stirring for 2 h, 91 mg of 2-chloropyrimidine was added. Stirring was continued for 42 h at room temperature. The solvent was evaporated and the remaining residue was partitioned between 50 ml of 10% aqueous acetic acid and 50 ml of ethyl acetate. The organic layer was separated and the aqueous layer was extracted two more times with 50 ml of ethyl acetate. The combined organic layers were washed with water and brine, dried over MgSO$_4$ and evaporated. The remaining residue was purified by column chromagraphy on silica gel eluting with a gradient of 5–10% of methanol in DCM. This furnished 256 mg of 4-tert.-butyl-N-[6-(4-(2-pyrimidinyloxy)-2-butynyloxy)-5-(o-methoxyphenoxy)-2-(4-pyridyl)-4-pyrimidinyl]-benzene sulfonamide as a colourless foam. LC-MS: $t_R$=5.21 min, [M+1]$^+$=653.69, [M−1]$^-$=651.78.

Example 20

200 mg of 4-tert.-butyl-N-[6-(4-(5-bromo-2-pyrimidinyloxy)-2-butynyloxy)-5-(o-methoxyphenoxy)-2-(4-pyridyl)-4-pyrimidinyl]-benzene sulfonamide was obtained in the form of beige crystals starting from 196 mg of 4-tert.-butyl-N-[6-(4-hydroxy-2-butynyloxy)-5-(o-methoxyphenoxy)-2-(4-pyridyl)-4-pyrimidinyl]-benzene sulfonamide (Example 2c) and 73 mg of 5-bromo-2-chloropyrimidine following the procedure given in Example 19. However, the crude product was purified by crystallisation from a methanol isopropanol mixture. LC-MS: $t_R$=5.63 min, [M+1]$^+$=731.65, [M−1]$^-$=729.66.

Example 21

A suspension of 400 mg of 4-tert.-butyl-N-[6-(4-hydroxy-2-butynyloxy)-5-(o-methoxyphenoxy)-2-(4-pyridyl)-4-pyrimidinyl]-benzene sulfonamide (Example 2c), 116 mg of 4,6-dimethoxy-2-methyl-sulfonylpyrimidine and 147 mg of potassium carbonate in 15 ml of DMF was stirred at 90° C. for 16 h. Further 42 mg of 4,6-dimethoxy-2-methyl-sulfonylpyrimidine was added and stirring was continued at 90° C. for 24 h. Eventually, the solvent was removed in vacuo, and the resulting residue partitioned between 50 ml of 5% aqueous acetic acid and 50 ml of DCM. The organic layer was separated and the aqueous layer was extracted two more times with 50 ml of DCM. The combined organic layers were washed with water, dried over MgSO$_4$ and evaporated. The remaining oil was purified by column chromatography on silica gel eluting with toluene: ethyl acetate 4:1 to 1:1. The product obtained was recrystallised from ethyl acetate:diethyl ether to give 76 mg of 4-tert.-butyl-N-[6-(4-(4,6-dimethoxy-2-pyrimidinyloxy)-2-butynyloxy)-5-(o-methoxyphenoxy)-2-(4-pyridyl)-4-pyrimidinyl]-benzene sulfonamide as white crystals. LC-MS: $t_R$=5.84 min, [M+1]$^+$=713.35, [M−1]$^-$=711.45.

Example 22

To a suspension of 41 mg of a 55% sodium hydride dispersion in mineral oil in 5 ml of dry DMF and 5 ml of dry THF 200 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3e) was added. After stirring for 10 min, 47 mg of 2-chloropyrimidine was added. Stirring was continued for 20 h at room temperature. Then another 20 mg of 2-chloropyrimidine was added and stirring was continued for another 24 h. Eventually, the reaction mixture was poured onto 50 ml of 10% aqueous citric acid. The solution was extracted twice with 50 ml of ethyl acetate. The combined organic layers were twice washed with water, dried over MgSO$_4$ and evaporated. The remaining residue was purified by column chromagraphy on silica gel eluting with a gradient of 0–3% of methanol in DCM. This furnished 147 mg of 5-methyl-N-[6-(4-(2-pyrimidinyloxy)-2-butynyloxy)-5-(o-methoxyphenoxy)-2-(4-pyridyl)-4-pyrimidinyl]-2-pyridine sulfonamide as a pale yellow powder. LC-MS: $t_R$=4.26 min, [M+1]$^+$=612.29, [M−1]$^-$=610.43.

Example 23

65 mg of 5-methyl-N-[6-(4-(5-bromo-2-pyrimidinyloxy)-2-butynyloxy)-5-(o-methoxyphenoxy)-2-(4-pyridyl)-4-pyrimidinyl]-2-pyridine sulfonamide was obtained as a pale yellow solid starting from 100 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3e) and 44 mg of 5-bromo-2-chloropyrimidine following the procedure given in Example 22. LC-MS: $t_R$=4.77 min, [M+1]$^+$=690.22, [M−1]$^-$=688.36.

Example 24

91 mg of 5-methyl-N-[6-(4-(4,6-dimethoxy-2-pyrimidinyloxy)-2-butynyloxy)-5-(o-methoxyphenoxy)-2-(4-pyridyl)-4-pyrimidinyl]-2-pyridine sulfonamide was obtained as a pale yellow solid starting from 100 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3e) and 82 mg of 4,6-dimethoxy-2-methylsulfonylpyrimidine following the procedure given in Example 22. LC-MS: $t_R$=4.80 min, [M+1]$^+$=672.32, [M−1]$^-$=670.46.

Example 25

72 mg of 5-methyl-N-[6-(4-(4,6-dimethyl-2-pyrimidinyloxy)-2-butynyloxy)-5-(o-methoxyphenoxy)-2-(4-pyridyl)4-pyrimidinyl]-2-pyridine sulfonamide was obtained as a pale yellow solid starting from 80 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3e) and 70 mg of 4,6-dimethyl-2-methylsulfonylpyrimidine following the procedure given in Example 22. LC-MS: $t_R$=4.68 min, [M+1]$^+$=640.32, [M−1]$^-$=638.39.

Example 26

59 mg of 5-isopropyl-N-[6-(4-(2-pyrimidinyloxy)-2-butynyloxy)-5-(o-methoxyphenoxy)-2-(2-pyrimidinyl)$_4$-pyrimidinyl]-2-pyridine sulfonamide was obtained as a beige foam starting from 80 mg of 5-isopropyl-N-[6-(4-hydroxy-2-butynyloxy)-5-(o-methoxyphenoxy)-2-(2-pyrimidinyl)4-pyrimidinyl]-2-pyridine sulfonamide (Example 4d) and 33 mg of 2-chloropyrimidine following the procedure given in Example 22. LC-MS: $t_R$=4.55 min, $[M+1]^+$=641.63, $[M-1]^-$=639.47.

Example 27

78 mg of 5-isopropyl-N-[6-(4-(5-bromo-2-pyrimidinyloxy)-2-butynyloxy)-5-(o-methoxy-phenoxy)-2-(2-pyrimidinyl)-4-pyrimidinyl]-2-pyridine sulfonamide was obtained as a beige foam starting from 80 mg of 5-isopropyl-N-[6-(4-hydroxy-2-butynyloxy)-5-(o-methoxyphenoxy)-2-(2-pyrimidinyl)-4-pyrimidinyl]-2-pyridine sulfonamide (Example 4d) and 55 mg of 5-bromo-2-chloropyrimidine following the procedure given in Example 22. LC-MS: $t_R$=4.99 min, $[M+1]^+$=719.56, $[M-1]^-$=717.28.

Example 28

65 mg of 4-tert.-butyl-N-[6-(4-(5-bromo-2-pyrimidinyloxy)-2-butynyloxy)-5-(o-methoxyphenoxy)-2-(2-pyrimidinyl)-4-pyrimidinyl]-benzene sulfonamide was obtained as a beige foam starting from 75 mg of 4-tert.-butyl-N-[6-(4-hydroxy-2-butynyloxy)-5-(o-methoxyphenoxy)-2-(2-pyrimidinyl)-4-pyrimidinyl]-benzene sulfonamide (Example 5b) and 103 mg of 5-bromo-2-chloropyrimidine following the procedure given in Example 22. LC-MS: $t_R$=5.83 min, $[M+1]^+$=732.31, $[M-1]^-$=730.36.

Example 29

71 mg of 4-tert.-butyl-N-[6-(4-(4,6-dimethoxy-2-pyrimidinyloxy)-2-butynyloxy)-5-(o-methoxyphenoxy)-2-(2-pyrimidinyl)-4-pyrimidinyl]-benzene sulfonamide was obtained as a colourless foam starting from 75 mg of 4-tert.-butyl-N-[6-(4-hydroxy-2-butynyloxy)-5-(o-methoxyphenoxy)-2-(2-pyrimi-dinyl)-4-pyrimidinyl]-benzene sulfonamide (Example 5b) and 140 mg of 4,6-dimethoxy-2-methylsulfonylpyrimidine following the procedure given in Example 22. LC-MS: $t_R$=5.92 min, $[M+1]^+$=714.42, $[M-1]^-$=712.50.

Example 30

20 mg of 5-methyl-N-[6-(4-(2-pyrimidinyloxy)-2-butynyloxy)-5-(o-methoxyphenoxy)-2-(2-pyrimidinyl)-4-pyrimidinyl]-2-pyridine sulfonamide was obtained as a colourless foam starting from 60 mg of 5-methyl-N-[6-(4-hydroxy-2-butynyloxy)-5-(o-methoxyphenoxy)-2-(2-pyrimidinyl)4-pyrimidinyl]-2-pyridine sulfonamide (Example 6b) and 36 mg of 2-chloropyrimidine following the procedure given in Example 22. LC-MS: $t_R$=4.37 min, $[M+1]^+$=613.29, $[M-1]^-$=611.45.

Example 31

75 mg of 5-methyl-N-[6-(4-(5-bromo-2-pyrimidinyloxy)-2-butynyloxy)-5-(o-methoxy-phenoxy)-2-(2-pyrimidinyl)-4-pyrimidinyl]-2-pyridine sulfonamide was obtained as a colourless powder starting from 80 mg of 5-methyl-N-[6-(4-hydroxy-2-butynyloxy)-5-(o-methoxyphenoxy)-2-(2-pyrimidinyl)-4-pyrimidinyl]-2-pyridine sulfonamide (Example 6b) and 120 mg of 5-bromo-2-chloropyrimidine following the procedure given in Example 22. LC-MS: $t_R$=4.64 min, $[M+1]^+$=691.64, $[M-1]^-$=689.45.

Example 32

84 mg of 5-methyl-N-[6-(4-(4,6-dimethoxy-2-pyrimidinyloxy)-2-butynyloxy)-5-(o-methoxy-phenoxy)-2-(2-pyrimidinyl)-4-pyrimidinyl]-2-pyridine sulfonamide was obtained as a colourless powder starting from 80 mg of 5-methyl-N-[6-(4-hydroxy-2-butynyloxy)-5-(o-methoxyphenoxy)-2-(2-pyrimidinyl)$_4$-pyrimidinyl]-2-pyridine sulfonamide (Example 6b) and 65 mg of 4,6-dimethoxy-2-methylsulfonylpyrimidine following the procedure given in Example 22. LC-MS: $t_R$=4.72 min, $[M+1]^+$=673.70, $[M-1]^-$=671.53.

Example 33

73 mg of 5-isopropyl-N-[6-(4-(2-pyrimidinyloxy)-2-butynyloxy)-5-(o-methoxyphenoxy)-2-methyl-4-pyrimidinyl]-2-pyridine sulfonamide was obtained as a colourless foam starting from 80 mg of 5-isopropyl-N-[6-(4-hydroxy-2-butynyloxy)-5-(o-methoxyphenoxy)-2-methyl-4-pyrimidinyl]-2-pyridine sulfonamide (Example 7d) and 46 mg of 2-chloropyrimidine following the procedure given in Example 17. LC-MS: $t_R$=5.18 min, $[M+1]^+$=577.27, $[M-1]^-$=575.36.

Example 34

75 mg of 5-isopropyl-N-[6-(4-(4,6-dimethoxy-2-pyrimidinyloxy)-2-butynyloxy)-5-(o-methoxyphenoxy)-2-methyl-4-pyrimidinyl]-2-pyridine sulfonamide was obtained as a colourless foam starting from 80 mg of 5-isopropyl-N-[6-(4-hydroxy-2-butynyloxy)-5-(o-methoxyphenoxy)-2-methyl-4-pyrimidinyl]-2-pyridine sulfonamide (Example 7d) and 88 mg of 4,6-dimethoxy-2-methylsulfonylpyrimidine following the procedure given in Example 17. LC-MS: $t_R$=5.80 min, $[M+1]^+$=637.31, $[M-1]^-$=635.40.

Example 35

76 mg of 5-isopropyl-N-[6-(4-(4,6-dimethyl-2-pyrimidinyloxy)-2-butynyloxy)-5-(o-methoxyphenoxy)-2-methyl-4-pyrimidinyl]-2-pyridine sulfonamide was obtained as a colourless foam starting from 80 mg of 5-isopropyl-N-[6-(4-hydroxy-2-butynyloxy)-5-(o-methoxyphenoxy)-2-methyl-4-pyrimidinyl]-2-pyridine sulfonamide (Example 7d) and 75 mg of 4,6-dimethyl-2-methylsulfonylpyrimidine following the procedure given in Example 17. LC-MS: $t_R$=5.51 min, $[M+1]^+$=605.35, $[M-1]^-$=603.43.

Example 36

98 mg of 5-methyl-N-[6-(4-(5-bromo-2-pyrimidinyloxy)-2-butynyloxy)-5-(o-methoxy-phenoxy)-2-methyl-4-pyrimidinyl]-2-pyridine sulfonamide was obtained as a colourless foam starting from 80 mg of 5-methyl-N-[6-(4-hydroxy-2-butynyloxy)-5-(o-methoxyphenoxy)-2-methyl-4-pyrimidinyl]-2-pyridine sulfonamide (Example 8b) and 96 mg of 5-bromo-2-chloropyrimidine following the procedure given in Example 22. LC-MS: $t_R$=5.33 min, $[M+1]^+$=627.20, $[M-1]^-$=625.27.

Example 37

80 mg of 5-methyl-N-[6-(4-(4,6-dimethoxy-2-pyrimidinyloxy)-2-butynyloxy)-5-(o-methoxy-phenoxy)-2-methyl-4-pyrimidinyl]-2-pyridine sulfonamide was obtained as a colourless foam starting from 80 mg of 5-methyl-N-[6-(4-hydroxy-2-butynyloxy)-5-(o-methoxyphenoxy)-2-methyl4-pyrimidinyl]-2-pyridine sulfonamide (Example 8b) and 74 mg of 4,6-dimethoxy-2-methylsulfonylpyrimidine following the procedure given in Example 22. LC-MS: $t_R$=5.46 min, $[M+1]^+$=609.31, $[M-1]^-$=607.38.

Example 38

80 mg of 5-methyl-N-[6-(4-(4,6-dimethyl-2-pyrimidinyloxy)-2-butynyloxy)-5-(o-methoxy-phenoxy)-2-methyl-4-pyrimidinyl]-2-pyridine sulfonamide was obtained as a colourless foam starting from 80 mg of 5-methyl-N-[6-(4-hydroxy-2-butynyloxy)-5-(o-methoxyphenoxy)-2-methyl-4-pyrimidinyl]-2-pyridine sulfonamide (Example 8b) and 79 mg of 4,6-dimethyl-2-methylsulfonylpyrimidine following the procedure given in Example 22. LC-MS: $t_R$=5.10 min, [M+1]$^+$=577.30, [M−1]$^-$=575.41.

Example 39

To a suspension of 58 mg of a 55% sodium hydride dispersion in mineral oil in 15 ml of dry THF 280 mg of 4-tert.-butyl-N-[6-(4-hydroxy-2-butynyloxy)-5-(p-tolyl)-4-pyrimidinyl]-benzene sulfonamide (Example 12) was added. After stirring for 1 h, 144 mg of 4,6-dimethoxy-2-methylsulfonylyrimidine was added. Stirring was continued for 12 h at reflux. Eventually, the solvent was evaporated and the remaining residue was partitioned between 50 ml of 10% aqueous citric acid and 50 ml of ethyl acetate. The organic layer was separated and the aqueous layer was extracted two more times with 50 ml of ethyl acetate. The combined organic layers were washed with water and brine, dried over MgSO$_4$ and evaporated. The remaining residue was purified by column chromagraphy on silica gel eluting with a gradient of 10–20% of ethyl acetate in toluene. The isolated yellow foam was further purified on a preparative silica gel plate. This furnished 91 mg of 4-tert.-butyl-N-[6-(4-(4,6-dimethoxy-2-pyrimidinyloxy)-butynyloxy)-5-(p-tolyl)-4-pyrimidinyl]-benzene sulfonamide as a colourless foam. LC-MS: $t_R$=6.32 min, [M+1]$^+$=604.31, [M−1]$^-$=602.43.

Example 40

To a suspension of 88 mg of a 55% sodium hydride dispersion in mineral oil in 15 ml of dry THF 375 mg of 4-tert.-butyl-N-[6-(4-hydroxy-2-butynyloxy)-5-(p-tolyl)-4-pyrimidinyl]-benzene sulfonamide (Example 12) was added. After stirring for 1 h, 170 mg of 5-bromo-2-chloropyrimidine was added. Stirring was continued for 60 h at 40° C. Eventually, the solvent was evaporated and the remaining residue was partitioned between 50 ml of 10% aqueous citric acid and 50 ml of ethyl acetate. The organic layer was separated and the aqueous layer was extracted two more times with 50 ml of ethyl acetate. The combined organic layers were washed with water and brine, dried over MgSO$_4$ and evaporated. The crude product was crystallised from 2-propanol containing a small amount of diethyl ether to give 168 mg of 4-tert.-butyl-N-[6-(4-(5-bromo-2-pyrimidinyloxy)-butynyloxy)-5-(p-tolyl)-4-pyrimidinyl]-benzene sulfonamide as beige crystals. LC-MS: $t_R$=6.22 min, [M+1]$^+$=624.28.

Example 41

To a suspension of 29 mg of a 55% sodium hydride dispersion in mineral oil in 15 ml of dry THF 150 mg of 4-tert.-butyl-N-[6-(4-hydroxy-2-butynyloxy)-5-(o-methoxy-phenoxy)-4-pyrimidinyl]-benzene sulfonamide (Example 10) was added. After stirring for 0.5 h, 64 mg of 5-bromo-2-chloropyrimidine was added. Stirring was continued for 40 h at 40° C. Eventually, the solvent was evaporated and the remaining residue was partitioned between 50 ml of 10% aqueous citric acid and 50 ml of ethyl acetate. The organic layer was separated and the aqueous layer was extracted two more times with 50 ml of ethyl acetate. The combined organic layers were washed with water and brine, dried over MgSO$_4$ and evaporated. The crude product was crystallised from 2-propanol to give 126 mg of 4-tert.-butyl-N-[6-(4-(5-bromo-2-pyrimidinyloxy)-2-butynyloxy)-5-(o-methoxy-phenoxy)-4-pyrimidinyl]-benzene sulfonamide as beige crystals. LC-MS: $t_R$=6.07 min, [M+1]$^+$=656.24, [M−1]$^+$=654.34.

Example 42

126 mg of 4-tert.-butyl-N-[6-(4-(4,6-dimethoxy-2-pyrimidinyloxy)-2-butynyloxy)-5-(o-methoxy-phenoxy)-4-pyrimidinyl]-benzene sulfonamide was obtained as a colourless foam starting from 150 mg of 4-tert.-butyl-N-[6-(4-hydroxy-2-butynyloxy)-5-(o-methoxy-phenoxy)-4-pyrimidinyl]-benzene sulfonamide (Example 10) and 72 mg of 4,6-dimethoxy-2-methylsulfonylpyrimidine following the procedure given in Example 41. LC-MS: $t_R$=6.13 min, [M+1]$^+$=635.81, [M−1]$^-$=633.77.

Example 43

To a suspension of 243 mg of K$_2$CO$_3$ in 15 ml of DMF 450 mg of 5-isopropyl-N-[6-(4-hydroxy-2-butynyloxy)-5-(p-tolyl)-2-(4-pyridyl)-4-pyrimidinyl]-2-pyridine sulfonamide (Example 11) was added. After stirring for 0.5 h at 90° C., 192 mg of 4,6-dimethoxy-2-methylsulfonylpyrimidine was added and stirring was continued for 16 h at 90° C. Eventually, the solvent was evaporated and the remaining residue was partitioned between 50 ml of 10% aqueous acetic acid and 50 ml of DCM. The organic layer was separated and the aqueous layer was extracted two more times with 50 ml of DCM. The combined organic layers were washed with water and brine, dried over MgSO$_4$ and evaporated. The crude product was purified by column chromatography on silica gel eluting with DCM:methanol 20:1 to give 88 mg of 5-isopropyl-N-[6-(4-(4,6-dimethoxy-2-pyrimidinyloxy)-2-butynyloxy)-5-(p-tolyl)-2-(4-pyridyl)-4-pyrimidinyl]-2-pyridine sulfonamide as a beige foam. LC-MS: $t_R$=5.54 min, [M+1]$^+$=668.38, [M−1]$^+$=666.39.

Example 44

186 mg of 5-isopropyl-N-[6-(4-(5-bromo-2-pyrimidinyloxy)-2-butynyloxy)-5-(o-methoxyphenoxy)-4-pyrimidinyl]-2-pyridine sulfonamide was obtained as beige crystals starting from 250 mg of 5-isopropyl-N-[6-(4-hydroxy-2-butynyloxy)-5-(o-methoxyphenoxy)-4-pyrimidinyl]-2-pyridine sulfonamide (Example 13) and 194 mg of 5-bromo-2-chloropyrimidine following the procedure given in Example 41. LC-MS: $t_R$=5.43 min, [M+1]$^+$=643.18, [M−1]$^-$=641.29.

Example 45

To a solution of 250 mg of 5-isopropyl-N-[6-(4-hydroxy-2-butynyloxy)-5-(o-methoxyphenoxy)-4-pyrimidinyl]-2-pyridine sulfonamide (Example 13) in 15 ml of THF was added 48 mg of NaH. The mixture was stirred for 2 h at room temperature before 120 mg of 4,6-dimethoxy-2-methylsulfonylpyrimidine was added. Stirring was continued for 16 h at reflux. Eventually, the solvent was evaporated and the remaining residue was partitioned between 50 ml of 10% aqueous citric acid and 50 ml of ethyl acetate. The organic layer was separated and the aqueous layer was extracted two more times with 50 ml of ethyl acetate. The combined organic layers were washed with water and brine, dried over MgSO$_4$ and evaporated. The crude product was purified by chromatography on prep. tlc-plates coated with silica gel with ethyl acetate:methanol: sat. aqueous ammonia 8:2:1 to give 71 mg of 5-isopropyl-N-[6-(4-(4,6-dimethoxy-2-pyrimidinyloxy)-2-butynyloxy)-5-(o-methoxyphenoxy)-4-pyrimidinyl]-2-pyridine sulfonamide as a beige foam. LC-MS: $t_R$=5.50 min, [M+1]$^+$=623.29, [M−1]$^+$=621.40.

Example 46

To a suspension of 9 mg of NaH 55% dispersion in mineral oil in 4 ml of DMF:THF 1:1 was added 50 mg of 4-tert.-butyl-N-[6-(4-hydroxy-2-butynyloxy)-5-(2-methoxy-phenoxy)-2-morpholin-4-yl-pyrimidin-4-yl]-benzene sulfonamide (Example 14). After the evolution of gas had ceased, 42 mg of 5-bromo-2-chloropyrimidine was added and the mixture was stirred for 1 h at 650C before it was diluted with 50 ml of 10% aqueous citric acid and 50 ml of ethyl acetate. The organic layer was separated, washed with 50 ml of water, dried over MgSO$_4$ and evaporated. The crude product was purified by column chromatography on silica gel eluting with hexane:ethyl acetate 3:2 to give 60 mg of 4-tert.-butyl-N-[6-(4-(5-bromo-2-pyrimidinyloxy)-2-butynyloxy)-5-(2-methoxy-phenoxy)-2-morpholin-4-yl-pyrimidin-4-yl]-benzene sulfonamide as a colourless foam. MS: $t_R$=6.14 min, [M+1]$^+$=739.18, [M−1]$^+$=741.32.

Example 47

48 mg of 4-tert.-butyl-N-[6-(4-(4,6-dimethoxy-2-pyrimidinyloxy)-2-butynyloxy)-5-(2-methoxy-phenoxy)-2-morpholin-4-yl-pyrimidin-4-yl]-benzene sulfonamide was obtained as a colourless foam starting from 50 mg of 4-tert.-butyl-N-[6-(4-hydroxy-2-butynyloxy)-5-(2-methoxy-phenoxy)-2-morpholin-4-yl-pyrimidin-4-yl]-benzene sulfonamide (Example 14) and 47 mg of 4,6-dimethoxy-2-methylsulfonylpyrimidine following the procedure given in Example 46. LC-MS: $t_R$=6.21 min, [M+1]$^+$=721.44, [M−1]$^+$=719.35

Example 48

37 mg of 5-methyl-N-[6-(4-(5-bromo-2-pyrimidinyloxy)-2-butynyloxy)-5-(2-methoxyphenoxy)-2-(N-morpholino)-4-pyrimidinyl]-2-pyridine sulfonamide was obtained as a beige powder starting from 50 mg of 5-methyl-N-[6-(4-hydroxy-2-butynyloxy)-5-(2-methoxyphenoxy)-2-(N-morpholino)-4-pyrimidinyl]-2-pyridine sulfonamide (Example 15) and 45 mg of 5-bromo-2-chloropyrimidine following the procedure given in Example 46. LC-MS: $t_R$=5.31 min, [M+1]$^+$=700.34, [M−1]$^+$=698.24.

Example 49

48 mg of 5-methyl-N-[6-(4-(4,6-dimethoxy-2-pyrimidinyloxy)-2-butynyloxy)-5-(2-methoxyphenoxy)-2-(N-morpholino)-4-pyrimidinyl]-2-pyridine sulfonamide was obtained as a colourless solid starting from 50 mg of 5-methyl-N-[6-(4-hydroxy-2-butynyloxy)-5-(2-methoxyphenoxy)-2-(N-morpholino)-4-pyrimidinyl]-2-pyridine sulfonamide (Example 15) and 50 mg of 4,6-dimethoxy-2-methylsulfonylpyrimidine following the procedure given in Example 46. LC-MS: $t_R$=5.42 min, [M+1]$^+$=680.43, [M−1]$^+$=678.36.

Example 50

128 mg of 5-isopropyl-N-[6-(4-(5-bromo-2-pyrimidinyloxy)-2-butynyloxy)-5-(p-tolyl)-4-pyrimidinyl]-2-pyridine sulfonamide was obtained as a beige foam starting from 230 mg of 5-isopropyl-N-[6-(4-hydroxy-2-butynyloxy)-5-(p-tolyl)-4-pyrimidinyl]-2-pyridine sulfonamide (Example 16) and 194 mg of 5-bromo-2-chloropyrimidine following the procedure given in Example 45. LC-MS: $t_R$=5.49 min, [M+1]$^+$=611.25, [M−1]$^+$=609.39.

Example 51

68 mg of 5-isopropyl-N-[6-(4-(4,6-dimethoxy-2-pyrimidinyloxy)-2-butynyloxy)-5-(p-tolyl)-4-pyrimidinyl]-2-pyridine sulfonamide was obtained as a beige foam starting from 230 mg of 5-isopropyl-N-[6-(4-hydroxy-2-butynyloxy)-5-(p-tolyl)-4-pyrimidinyl]-2-pyridine sulfonamide (Example 16) and 120 mg of 4,6-dimethoxy-2-methylsulfonylpyrimidine following the procedure given in Example 45. LC-MS: $t_R$=5.60 min, [M+1]$^+$=591.21, [M−1]$^+$=589.24.

Example 52

To a solution of 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 10 mg of 4-dimethylaminopyridine in 5 ml of dry chloroform 25 µl of n-butyl isocyanate was added at room temperature. The mixture was heated to 65° C. and stirred for 42 h. After 6 h, 18 h, and 28 h another portion of 25 µl of n-butyl isocyanate was added. Eventually, the mixture was diluted with 50 ml of ethyl acetate. The solution was washed twice with 20 ml of water. The aqueous layers were extracted once with ethyl acetate. The combined organic layers were dried over MgSO$_4$ and evaporated. The residue was purified by column chromatography on silica gel eluting first with hexane:ethyl acetate 1:1 then with DCM containing 4% of methanol. This gave 39 mg of n-butyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester as a pale yellow foam. LC-MS: $t_R$=5.17 min, [M+1]$^+$=661.37, [M−1]$^-$=659.51.

Example 53

To a solution of 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 10 mg of 4-dimethylaminopyridine in 5 ml of dry chloroform 25 µl of phenyl isocyanate was added at room temperature. The mixture was heated to 65° C. and stirred for 4 h. Eventually, the mixture was diluted with 50 ml of ethyl acetate. The solution was washed twice with 20 ml of water. The aqueous layers were extracted once with ethyl acetate. The combined organic layers were dried over MgSO$_4$ and evaporated. The residue was purified by column chromatography on silica gel eluting first with hexane:ethyl acetate 1:1 then with DCM containing 4% of methanol. This gave 40 mg of phenyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester as an off-white solid which melts at 163–164° C. LC-MS: $t_R$=5.15 min, [M+1]$^+$=681.36, [M−1]$^-$=679.51.

Example 54

39 mg of m-tolyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester was obtained as an off-white solid starting from 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 25 µl of m-tolyl isocyanate

Example 55

45 mg of (4-methoxyphenyl)-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester was obtained as a pale yellow foam starting from 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 25 µl of 4-methoxyphenyl isocyanate following the procedure given in Example 53. LC-MS: $t_R$=5.06 min, [M+1]$^+$=711.35, [M−1]$^−$=709.48.

Example 56

27 mg of (2-methoxy-phenyl)-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester was obtained as a pale yellow foam starting from 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 25 µl of 2-methoxyphenyl isocyanate following the procedure given in Example 53. LC-MS: $t_R$=5.30 min, [M+1]$^+$=711.36, [M−1]$^−$=709.49.

Example 57

36 mg of (2-fluorophenyl)-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester was obtained as a white solid starting from 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 12 mg of 2-fluorophenyl isocyanate following the procedure given in Example 53. LC-MS: $t_R$=5.16 min, [M+1]$^+$=699.36, [M−1]$^−$=697.28.

Example 58

A solution of 50 mg of 2-picolinic acid azide (prepared from 2-picolinic acid according to Chem. Pharm. Bull. 25 (1977) 1651–1657) and 10 mg of DMAP in 8 ml of chloroform was stirred for 1 h at 75° C. 50 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) followed by 3 ml of DMF was added and the resulting clear solution was stirred for 16 h at 75° C. The mixture was diluted with 75 ml of ethyl acetate and washed with 50 ml of 10% aqueous citric acid followed by 50 ml of water. The organic layer was evaporated and the crude product was purified by chromatography on prep. tlc-plates with dichlormethane:methanol 10:1 to give 41 mg of 2-pyridinyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester as a white solid. LC-MS: $t_R$=4.74 min, [M+1]$^+$=682.47, [M−1]$^−$=680.41.

Example 59

271 mg of 2-pyrazinyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester was obtained as a white powder starting from 300 mg of 5-isopropyl-N-[6-(4-hydroxy-2-butynyloxy)-5-(o-methoxyphenoxy)-2-(4-pyridyl)-4-pyrimidinyl]-2-pyridine sulfonamide (Example 1g) and 199 mg of pyrazine-2-carbonyl azide (prepared from pyrazin-2-carboxylic acid according to Chem. Pharm. Bull. 25 (1977) 1651–1657) following the procedure given in Example 58. LC-MS: $t_R$=4.73 min, [M+1]$^+$=683.44, [M−1]$^−$=681.37.

Example 60

Under argon, a suspension of 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3), 10 mg of DMAP and 25 µl of cyclohexylisocyanate in 4 ml of chloroform and 3 ml of DMF was stirred for 72 h at 70° C. The mixture was diluted with 50 ml of ethyl acetate and washed with 50 ml of 10% aqueous citric acid and 2×25 mlf of water. The organic phase was dried over MgSO$_4$ and evaporated. The crude product was purified by column chromatography on silica gel eluting with a gradient of hexane:ethyl acetate 1:1 to ethyl acetate, then with DCM containing 4% of methanol to give 38 mg of cyclohexyl-carbamic acid 4-[6-(5-methylpyridine-2-sulfonylamino)-5-(2-methoxy-phenoxy)-2-pyridin-4-yl-pyrimidin-4-yloxy]-but-2-ynyl ester as a beige foam. LC-MS: $t_R$=4.89 min, [M+1]$^+$=659.33, [M−1]$^−$=657.25.

Example 61

A suspension of 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3), 10 mg of DMAP and 25 µl of phenylisocyanate in 5 ml of chloroform was refluxed for 15 minutes under argon. 1.5 ml of DMF was added and stirring and heating was continued for 16 h. The clear solution was diluted with 50 ml of ethyl acetate and washed with 50 ml of 10% aqueous citric acid and 2×50 ml of water. The organic phase was dried over MgSO$_4$ and evaporated. The crude product was purified by column chromatography on silica gel eluting first with hexane:ethyl acetate 1:1, then with DCM containing 4% of methanol to give 47 mg of phenylcarbamic acid 4-[6-(5-methylpyridine-2-sulfonylamino)-5-(2-methoxy-phenoxy)-2-pyridin-4-yl-pyrimidin-4-yloxy]-but-2-ynyl ester as a slightly yellow solid. LC-MS: $t_R$=4.80 min, [M+1]$^+$=653.37, [M−1]$^−$=651.33.

Example 62

37 mg of (3-methylphenyl)-carbamic acid 4-[6-(5-methylpyridine-2-sulfonylamino)-5-(2-methoxy-phenoxy)-2-pyridin-4-yl-pyrimidin-4-yloxy]-but-2-ynyl ester was obtained as a yellow solid starting from 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3) and 25 µl of 3-methylphenylisocyanate following the procedure given in Example 61. MS: $t_R$=4.95 min, [M+1]$^+$=667.42, [M−1]$^−$=665.30.

Example 63

38 mg of (2-fluorophenyl)-carbamic acid 4-[6-(5-methylpyridine-2-sulfonylamino)-5-(2-methoxy-phenoxy)-2-pyridin-4-yl-pyrimidin-4-yloxy]-but-2-ynyl ester was obtained as an off-white foam starting from 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3) and 25 µl of 2-fluorophenylisocyanate following the procedure given in Example 61. MS: $t_R$=4.79 min, [M+1]$^+$=671.34, [M−1]$^−$=669.28.

Example 64

42 mg of (4-fluorophenyl)-carbamic acid 4-[6-(5-methylpyridine-2-sulfonylamino)-5-(2-methoxy-phenoxy)-

2-pyridin-4-yl-pyrimidin-4-yloxy]-but-2-ynyl ester was obtained as an off-white foam starting from 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3) and 25 µl of 4-fluorophenylisocyanate following the procedure given in Example 61. MS: $t_R$=4.89 min, $[M+1]^+$=671.34, $[M-1]^-$=669.28.

Example 65

38 mg of 2-pyridinyl-carbamic acid 4-[6-(5-methyl-pyridine-2-sulfonylamino)-5-(2-methoxy-phenoxy)-2-pyridin-4-yl-pyrimidin-4-yloxy]-but-2-ynyl ester was obtained as a white powder starting from 50 mg of 5-methyl-N-[6-(4-hydroxy-2-butynyloxy)-5-(o-methoxyphenoxy)-2-(4-pyridyl)-4-pyrimidinyl]-2-pyridine sulfonamide (Example 3) and 50 mg of 2-picolinic acid azide (prepared from 2-picolinic acid according to Chem. Pharm. Bull. 25 (1977) 1651–1657) according to the procedure given in Example 58. MS: $t_R$=4.32 min, $[M+1]^+$=654.39, $[M-1]^-$=652.33.

Example 66

18 mg of 2-pyridinyl-carbamic acid 4-[6-(5-isopropyl-pyridine-2-sulfonylamino)-5-(2-methoxy-phenoxy)-2-(2-pyrimidinyl)-pyrimidin-4-yloxy]-but-2-ynyl ester was obtained as a white solid starting from 50 mg of 5-isopropyl-N-[6-(4-hydroxy-2-butynyloxy)-5-(o-methoxy-phenoxy)-2-(2-pyrimidinyl)-4-pyrimidinyl]-2-pyridine sulfonamide (Example 4) and 28 mg of 2-picolinic acid azide (prepared from 2-picolinic acid according to Chem. Pharm. Bull. 25 (1977) 1651–1657) according to the procedure given in Example 58. MS: $t_R$=4.84 min, $[M+1]^+$=683.41.

Example 67

28 mg of 2-pyrazinyl-carbamic acid 4-[6-(5-isopropyl-pyridine-2-sulfonylamino)-5-(2-methoxy-phenoxy)-2-(2-pyrimidinyl)-pyrimidin-4-yloxy]-but-2-ynyl ester was obtained as a slightly yellow solid starting from 50 mg of 5-isopropyl-N-[6-(4-hydroxy-2-butynyloxy)-5-(o-methoxy-phenoxy)-2-(2-pyrimidinyl)-4-pyrimidinyl]-2-pyridine sulfonamide (Example 4) and 50 mg of pyrazine-2-carbonyl azide (prepared from pyrazin-2-carboxylic acid according to Chem. Pharm. Bull. 25 (1977) 1651–1657) following the procedure given in Example 58. LC-MS: $t_R$=4.67 min, $[M+1]^+$=684.42, $[M-1]^-$=682.39.

Example 68

24 mg of 2-pyridinyl-carbamic acid 4-[6-(4-tert.butylbenzenesulfonylamino)-5-(2-methoxy-phenoxy)-2-(2-pyrimidinyl)-pyrimidin-4-yloxy]-but-2-ynyl ester was obtained as a slightly yellow solid starting from 50 mg of 4-tert.-butyl-N-[6-(4-hydroxy-2-butynyloxy)-5-(o-methoxy-phenoxy)-2-(2-pyrimidinyl)-4-pyrimidinyl] benzene sulfonamide (Example 5) and 50 mg of 2-picolinic acid azide (prepared from 2-picolinic acid according to Chem. Pharm. Bull. 25 (1977) 1651–1657) following the procedure given in Example 58. LC-MS: $t_R$=5.44 min, $[M+1]^+$=696.43, $[M-1]^-$=694.35.

Example 69

39 mg of 2-pyrazinyl-carbamic acid 4-[6-(4-tert.butylbenzenesulfonylamino)-5-(2-methoxy-phenoxy)-2-(2-pyrimidinyl)-pyrimidin-4-yloxy]-but-2-ynyl ester was obtained as a slightly yellow solid starting from 50 mg of 4-tert.-butyl-N-[6-(4-hydroxy-2-butynyloxy)-5-(o-methoxy-phenoxy)-2-(2-pyrimidinyl)-4-pyrimidinyl] benzene sulfonamide (Example 5) and 50 mg of pyrazine-2-carbonyl azide (prepared from pyrazin-2-carboxylic acid according to Chem. Pharm. Bull. 25 (1977) 1651–1657) following the procedure given in Example 58. LC-MS: $t_R$=5.25 min, $[M+1]^+$=697.44, $[M-1]^-$=695.35.

Example 70

To a solution of 50 mg of 5-isopropyl-N-[6-(4-hydroxy-2-butynyloxy)-5-(o-methoxyphenoxy)-2-methyl-4-pyrimidinyl]-2-pyridine sulfonamide (Example 7d) in 5 ml of dry chloroform 25 µl of phenyl isocyanate followed by 20 mg of DMAP was added. The solution was stirred at 65° C. for 3 h. The solvent was removed partially under reduced pressure and the remaining solution was purified by column chromatography on 20 g of silica gel eluting with hexane-:ethyl acetate 2:1. This gave 35 mg of phenyl-carbamic acid 4-[(6-(5-isopropyl-pyridine-2-sulfonylamino)-5-(2-methoxy-phenoxy)-2-methyl-pyrimidin-4-yloxy]-but-2-ynyl ester as a colourless foam. LC-MS: $t_R$=5.62 min, $[M+1]^+$=618.33, $[M-1]^-$=616.45.

Example 71

43 mg of phenyl-carbamic acid 4-[6-(5-isopropyl-pyridine-2-sulfonylamino)-5-(2-methoxy-phenoxy)-2-morpholin-4-yl-pyrimidin-4-yloxy]-but-2-ynyl ester was obtained as a white foam starting from 50 mg of 5-isopropyl-N-[6-(4-hydroxy-2-butynyloxy)-5-(o-methoxyphenoxy)-2-(N-morpholino)-4-pyrimidinyl]-2-pyridine sulfonamide (Example 9) and 30 µl of phenylisocyanate following the procedure given in Example 53. LC-MS: $t_R$=5.57 min, $[M+1]^+$=689.38, $[M-1]^-$=687.49.

Example 72

142 mg of 2-pyridinyl-carbamic acid 4-[6-(5-isopropyl-pyridine-2-sulfonylamino)-5-(2-methoxy-phenoxy)-2-(N-morpholino)-pyrimidin-4-yloxy]-but-2-ynyl ester was obtained as a colourless foam starting from 150 mg of 5-isopropyl-N-[6-(4-hydroxy-2-butynyloxy)-5-(o-methoxyphenoxy)-2-(N-morpholino)-4-pyrimidinyl]-2-pyridine sulfonamide (Example 9) and 100 mg of 2-picolinic acid azide (prepared from 2-picolinic acid according to Chem. Pharm. Bull. 25 (1977) 1651–1657) following the procedure given in Example 58. LC-MS: $t_R$=5.37 min, $[M+1]^+$=690.53, $[M-1]^-$=688.38.

Example 73

To a solution of 570 mg of 5-isopropyl-N-[6-(4-hydroxy-2-butynyloxy)-5-(o-methoxyphenoxy)-2-(N-morpholino)-4-pyrimidinyl]-2-pyridine sulfonamide (Example 9) in 15 ml of DCM was added 0.37 ml of DBU, a catalytic amount of DMAP and 70 µl of morpholine-4-carbonyl chloride. The mixture was stirred at reflux for 16 h before it was evaporated. The residue was partitioned between 75 ml of 10% aqueous citric acid and 75 ml of ethyl acetate. The aqueous phase was extracted two more times with ethyl acetate, the combined organic layers were washed with water and brine, dried over $MgSO_4$ and evaporated. The crude product was purified on prep. tlc-plates with toluene:ethyl acetate 1:1 to give 152 mg of morpholine-4-carbamic acid 4-[6-(5-isopropyl-pyridine-2-sulfonylamino)-5-(2-methoxy-phenoxy)-2-(N-morpholino)-pyrimidin-4-yloxy]-but-2-ynyl ester as a beige foam. LC-MS: $t_R$=5.26 min, $[M+1]^+$=683.43, $[M-1]^-$=681.57.

Example 74

170 mg of dimethyl-carbamic acid 4-[6-(5-isopropyl-pyridine-2-sulfonylamino)-5-(2-methoxy-phenoxy)-2-(N-morpholino)-pyrimidin-4-yloxy]-but-2-ynyl ester was obtained as white crystals (from 2-propanol/methanol) starting from 570 mg of 5-isopropyl-N-[6-(4-hydroxy-2-butynyloxy)-5-(o-methoxyphenoxy)-2-(N-morpholino)-4-pyrimidinyl]-2-pyridine sulfonamide (Example 9) and 52 µl of diemthylcarbamic acid chloride following the procedure given in Example 72. LC-MS: $t_R$=5.29 min, $[M+1]^+$=641.41, $[M-1]^-$=639.56.

Example 75

39 mg of phenyl-carbamic acid 4-[6-(5-isopropyl-pyridine-2-sulfonylamino)-5-(2-methoxy-phenoxy)-pyrimidin-4-yloxy]-but-2-ynyl ester was obtained as a colourless foam starting from 40 mg of 5-isopropyl-N-[6-(4-hydroxy-2-butynyloxy)-5-(o-methoxyphenoxy)-4-pyrimidinyl]-2-pyridine sulfonamide (Example 13) and 50 µl of phenylisocyanate following the procedure given in Example 53. LC-MS: $t_R$=5.38 min, $[M+1]^+$=604.32, $[M-1]^-$=602.25.

Example 76

50 mg of phenyl-carbamic acid 4-[6-(4-tert.-butyl-benzene-sulfonylamino)-5-(2-methoxy-phenoxy)-2-morpholin-4-yl-pyrimidin-4-yloxy]-but-2-ynyl ester was obtained as a colourless foam starting from 50 mg of 4-tert.-butyl-N-[6-(4-hydroxy-2-butynyloxy)-5-(2-methoxy-phenoxy)-2-morpholin-4-yl-pyrimidin-4-yl]-benzene sulfonamide (Example 14) and 50 µl of phenylisocyanate following the procedure given in Example 53. LC-MS: $t_R$=6.07 min, $[M+1]^+$=702.50, $[M-1]^-$=700.40.

Example 77

39 mg of 2-pyridinyl-carbamic acid 4-[6-(4-tert.-butyl-benzene-sulfonylamino)-5-(2-methoxy-phenoxy)-2-(N-morpholino)-pyrimidin-4-yloxy]-but-2-ynyl ester was obtained as a colourless foam starting from 50 mg of 4-tert.-butyl-N-[6-(4-hydroxy-2-butynyloxy)-5-(2-methoxy-phenoxy)-2-(N-morpholino)-pyrimidin-4-yl]-benzene sulfonamide (Example 14) and 50 mg of 2-picolinic acid azide (prepared from 2-picolinic acid according to Chem. Pharm. Bull. 25 (1977) 1651–1657) according to the procedure given in Example 58. MS: $t_R$=5.63 min, $[M+1]^+$=703.46, $[M-1]^-$=701.38.

Example 78

44 mg of n-butyl-carbamic acid 4-[6-(5-methyl-pyridine-2-sulfonylamino)-5-(2-methoxy-phenoxy)-2-(N-morpholino)-pyrimidin-4-yloxy]-but-2-ynyl ester was obtained as a white solid starting from 50 mg of 5-methyl-N-[6-(4-hydroxy-2-butynyloxy)-5-(2-methoxyphenoxy)-2-(N-morpholino)-4-pyrimidinyl]-2-pyridine sulfonamide (Example 15) and 50 µl of n-butylisocyanate according to the procedure given in Example 53. MS: $t_R$=5.24 min, $[M+1]^+$=641.47, $[M-1]^-$=639.39.

Example 79

53 mg of cyclohexyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a colourless foam starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 100 µl of cyclohexylisocyanate according to the procedure given in Example 53. MS: $t_R$=5.32 min, $[M+1]^+$=667.48, $[M-1]^-$=665.41.

Example 80

54 mg of phenyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a colourless foam starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 50 µl of phenylisocyanate according to the procedure given in Example 53. MS: $t_R$=5.32 min, $[M+1]^+$=661.43, $[M-1]^-$=659.38.

Example 81

36 mg of 2-pyridinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a white powder starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 50 mg of 2-picolinic acid azide (prepared from 2-picolinic acid according to Chem. Pharm. Bull. 25 (1977) 1651–1657) according to the procedure given in Example 58. MS: $t_R$=4.90 min, $[M+1]^+$=662.17, $[M-1]^-$=660.12.

Example 82

40 mg of 3-pyridinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a white powder starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 50 mg of nicotinic acid azide (prepared from nicotinic acid according to Chem. Pharm. Bull. 25 (1977) 1651–1657) according to the procedure given in Example 58. MS: $t_R$=4.19 min, $[M+1]^+$=662.39, $[M-1]^-$=660.59.

Example 83

7 mg of 4-pyridinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a white solid starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 50 mg of isonicotinic acid azide (prepared from isonicotinic acid according to Chem. Pharm. Bull. 25 (1977) 1651–1657) according to the procedure given in Example 58. MS: $t_R$=3.89 min, $[M+1]^+$=662.39, $[M-1]^-$=660.33.

Example 84

204 mg of 4-pyrazinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester was obtained as a white solid starting from 50 mg of 5-methyl-N-[6-(4-hydroxy-2-butynyloxy)-5-(2-methoxyphenoxy)-2-(4-morpholino)-4-pyrimidinyl]-2-pyridine sulfonamide (Example 15) and 50 mg of pyrazine-2-carbonyl azide (prepared from pyrazin-2-carboxylic acid according to Chem. Pharm. Bull. 25 (1977) 1651–1657) following the procedure given in Example 58. MS: $t_R$=4.80 min, $[M+1]^+$=663.43, $[M-1]^-$=661.36.

Example 85

36 mg of phenyl-carbamic acid 4-[6-(5-isopropyl-pyridine-2-sulfonylamino)-5-(p-tolyl)-pyrimidin-4-yloxy]-but-2-ynyl ester was obtained as an off-white foam starting from 60 mg of 5-isopropyl-N-[6-(4-hydroxy-2-butynyloxy)-5-(p-tolyl)-4-pyrimidinyl]-2-pyridine sulfonamide (Example 16) and 50 µl of phenylisocyanate following the procedure given in Example 53. MS: $t_R$=5.50 min, $[M+1]^+$=572.36, $[M-1]^-$=570.30.

Example 86

79 mg of N-methyl-N-phenyl-carbamic acid 4-[6-(5-isopropyl-pyridine-2-sulfonylamino)-5-(p-tolyl)-pyrimidin-4-yloxy]-but-2-ynyl ester was obtained as a beige foam starting from 230 mg of 5-isopropyl-N-[6-(4-hydroxy-2-butynyloxy)-5-(p-tolyl)-4-pyrimidinyl]-2-pyridine sulfonamide (Example 16) and 95 mg of N-methyl-N-phenyl-carbamic acid chloride following the procedure given in Example 72. LC-MS: $t_R$=5.44 min, $[M+1]^+$=586.33, $[M-1]^-$=584.50.

Example 87

To a solution of 300 mg of 5-isopropyl-N-[6-chloro-5-(o-methoxyphenoxy)-2-(4-pyridyl)$_4$-pyrimidinyl]-2-pyridine sulfonamide (Example 1f) and 1.47 g of 4-methoxy-2-butynol (prepared starting from 2-butyn-1,4-diol and dimethylsulfate following the procedure given in Bull. Chem. Soc. Japan 28 (1955), 80–83) in 15 ml of DMF was carefully added 234 mg of 55% NaH in mineral oil. The brown solution stirred for 24 h at room temperature before further 120 mg of 55% NaH in mineral oil was added. Stirring was continued for 24 h. The mixture was diluted with 100 ml of 10% aqueous citric acid and extracted four times with 50 ml of ethyl acetate. The combined organic phases were washed twice with 50 ml of water, dried over MgSO$_4$ and evaporated. The crude product was purified by column chromatography on silica gel eluting with ethyl acetate to give 154 mg of 5-isopropyl-N-[6-(4-methoxy-but-2-ynyloxy)-5-(2-methoxy-phenoxy)-2-pyridin-4-yl-pyrimidin-4-yl]-2-pyridine sulfonamide as a yellow solid. LC-MS: $t_R$=4.84 min, $[M+1]^+$=576.42, $[M-1]^-$=574.37.

Example 88

To a solution of 300 mg of 5-isopropyl-N-[6-chloro-5-(o-methoxyphenoxy)-2-(4-pyridyl)-4-pyrimidinyl]-2-pyridine sulfonamide (Example 1f) and 502 mg of 4-phenoxy-2-butyn-1-ol (prepared starting from phenyl-propargylether and para-formaldehyde following the procedure given in J. Chem. Soc. Perkin Trans. 1, 1991, 1721–1727) in 15 ml of THF was added 228 mg of 55% NaH in mineral oil. The orange suspension was stirred at room temperature for 1 h before it was diluted with 100 ml of 10% aqueous citric acid. The mixture was extracted three times with 50 ml of ethyl acetate. The combined organic phases were washed with 50 ml of water, dried over MgSO$_4$ and evaporated. The crude product was purified by prep. tlc-plates with ethyl acetate:methanol:sat. aqueous ammonia 8:2:1 to give 241 mg of 5-isopropyl-N-[6-(4-phenoxy-but-2-ynyloxy)-5-(2-methoxy-phenoxy)-2-pyrid in-4-yl-pyrimidin-4-yl]-2-pyridine sulfonamide as a slightly yellow foam. LC-MS: $t_R$=5.95 min, $[M+1]^+$=666.58, $[M-1]^-$=664.62

Example 89

To a mixture of 250 mg of 4-tert.-butyl-N-[6-chloro-5-(o-methoxyphenoxy)-2-(2-pyrimidinyl)-4-pyrimi-dinyl]benzene sulfonamide (Example 5a) and 1.11 g of 4-methoxy-2-butynol (prepared starting from 2-butyn-1,4-diol and dimethylsulfate following the procedure given in Bull. Chem. Soc. Japan 28 (1955), 80–83) in 15 ml THF was added 177 mg of 55% NaH in mineral oil. The suspension was stirred for 16 h at reflux. The reaction mixture was cooled, diluted with 100 ml 10% aqueous citric acid and extracted 4 times with 50 ml of ethyl acetate. The combined organic phases were washed with water, dried over MgSO$_4$ and evaporated. The crude product was purified by chromatography on prep. tlc-plates with ethyl acetate:methanol:sat. aqueous ammonia 8:2:1 to give 116 mg of 4-tert.-butyl-N-[6-(4-methoxy-2-butynyloxy)-5-(o-methoxy-phenoxy)-2-(2-pyrimidinyl)-4-pyrimidinyl]benzene sulfonamide as a slightly yellow foam. LC-MS: $t_R$=5.19 min, $[M+1]^+$=590.40, $[M-1]^-$=588.39

Example 90

To a mixture of 260 mg of 4-tert.-butyl-N-[6-chloro-5-(o-methoxyphenoxy)-2-(2-pyrimidinyl)-4-pyrimidinyl]benzene sulfonamide (Example 5a) and 1.50 g of 4-phenoxy-2-butyn-1-ol (prepared starting from phenyl-propargylether and para-formaldehyde following the procedure given in J. Chem. Soc. Perkin Trans. 1, 1991, 1721–1727) in 15 ml THF was added 184 mg of 55% NaH in mineral oil. The suspension was stirred for 1 h at reflux. The reaction mixture was cooled, diluted with 100 ml 10% aqueous citric acid and extracted 4 times with 50 ml of ethyl acetate. The combined organic phases were washed with water, dried over MgSO$_4$ and evaporated. The crude product was purified by chromatography on prep. tlc-plates with ethyl acetate:methanol:sat. aqueous ammonia 8:2:1 to give 82 mg of 4-tert.-butyl-N-[6-(4-phenoxy-2-butynyloxy)-5-(o-methoxy-phenoxy)-2-(2-pyrimidinyl)-4-pyrimidinyl]benzene sulfonamide as a slightly yellow foam. LC-MS: $t_R$=5.60 min, $[M+1]^+$=652.63, $[M-1]^-$=650.58.

Example 91

To a solution of 390 mg of 4-benzyloxy-2-butyn-1-ol (prepared starting from 2-butyn-1,4-diol and benzylbromide in analogy to a procedure reported in Tetrahedron Left. 38 (1997), 7887–7890) in 5 ml DMF:THF 1:1 was added 97 mg of 55% NaH in mineral oil. After the evolution of gas had ceased, 250 mg of 4-tert.-butyl-N-[6-chloro-5-(o-methoxyphenoxy)-2-(2-pyrimidinyl)4-pyrimidinyl]benzene sulfonamide (Example 5a) was added and the mixture was stirred at 50° C. for 20 h before it was diluted with 75 ml of ethyl acetate. The mixture was washed with 75 ml of 10% aqueous citric acid and 75 ml of water, and evaporated. The crude product was purified by chromatography on prep. tlc-plates with ethyl acetate:methanol:sat. aqueous ammonia 10:2:1 to give 125 mg of 4-tert.-butyl-N-[6-(4-benzyloxy-2-butynyloxy)-5-(o-methoxyphenoxy)-2-(2-pyrimidinyl)-4-pyrimidinyl]benzene sulfonamide as a yellow foam. LC-MS: $t_R$=5.93 min, $[M+1]^+$=666.47, $[M-1]^-$=664.63.

Example 92

184 mg of 4-tert.-butyl-N-[6-(4-(4-methylbenzyloxy)-2-butynyloxy)-5-(o-methoxy-phenoxy)-2-(2-pyrimidinyl)-4-pyrimidinyl]benzene sulfonamide was obtained as a yellow foam starting from 250 mg of 4-tert.-butyl-N-[6-chloro-5-(o-methoxyphenoxy)-2-(2-pyrimidinyl)-4-pyrimidinyl]

benzene sulfonamide (Example 5a) and 421 mg of 4-(4-methylbenzyloxy)-2-butyn-1-ol (prepared starting from 2-butyn-1,4-diol and 4-methylbenzylbromide in analogy to a procedure reported in Tetrahedron Lett. 38 (1997), 7887–7890) following the procedure given in Example 91. LC-MS: $t_R$=6.11 min, [M+1]$^+$=680.51, [M−1]$^-$=678.61.

Example 93

Crude 4-tert.-butyl-N-[6-(4-(3-methoxybenzyloxy)-2-butynyloxy)-5-(o-methoxyphenoxy)-2-(2-pyrimidinyl)-4-pyrimidinyl]benzene sulfonamide was obtained starting from 300 mg of 4-tert.-butyl-N-[6-chloro-5-(o-methoxyphenoxy)-2-(2-pyrimidinyl)-4-pyrimidinyl] benzene sulfonamide (Example 5a) and 1096 mg of 4-(3-methoxybenzyloxy)-2-butyn-1-ol (prepared starting from 2-butyn-1,4-diol and 3-methoxybenzylbromide in analogy to a procedure reported in Tetrahedron Lett. 38 (1997), 7887–7890) following the procedure given in Example 91. The compound was purified by column chromatography on silica gel eluting with DCM containing 0–2.5% of methanol followed by chromatography on prep. tlc-plates with DCM containing 5% of methanol. The resulting oil was dissolved in 10 ml of diethyl ether and treated with pentane. The precipitate was collected and dried to give 102 mg of 4-tert.-butyl-N-[6-(4-(3-methoxybenzyloxy)-2-butynyloxy)-5-(o-methoxy-phenoxy)-2-(2-pyrimidinyl)-4-pyrimidinyl]benzene sulfonamide as an almost white powder. LC-MS: $t_R$=5.74 min, [M+1]$^+$=696.40, [M−1]$^-$=694.32.

Example 94

To a mixture of 250 mg of 5-isopropyl-N-[6-chloro-5-(o-methoxyphenoxy)-2-(N-morpholino)-4-pyrimidinyl]-2-pyridine sulfonamide (Example 9c) and 1.2 g of 4-methoxy-2-butyn-1-ol (prepared starting from 2-butyn-1,4-diol and dimethylsulfate following the procedure given in Bull. Chem. Soc. Japan 28 (1955), 80–83) was added 192 mg of 55% NaH in mineral oil. After evolution of gas had ceased, the brown suspension was refluxed for 16 h. Further 96 mg of 55% NaH in mineral oil was added and heating and stirring was continued for another 3 h. The mixture was cooled, diluted with 50 ml of 10% aqueous citric acid and extracted 4 times with 50 ml of ethyl acetate. The combined organic phases were washed with water, dried over MgSO$_4$ and evaporated. The crude product was purified by column chromatography on silica gel eluting with hexane:ethyl acetate 1:3 and precipitated from diethyl ether to give 114 mg of 5-isopropyl-N-[6-(4-methoxy-2-butynyloxy)-5-(o-methoxyphenoxy)-2-(N-morpholino)-4-pyrimidinyl]-2-pyridine sulfonamide as a white powder. LC-MS: $t_R$=5.19 min, [M+1]$^+$=584.46, [M−1]$^-$=582.38.

Example 95

To a mixture of 300 mg of 4-tert.-butyl-N-[6-chloro-5-(p-tolyl)-4-pyrimidinyl]-benzene sulfonamide (Example 12c) and 1.8 g of 4-methoxy-2-butyn-1-ol (prepared starting from 2-butyn-1,4-diol and dimethylsulfate following the procedure given in Bull. Chem. Soc. Japan 28 (1955), 80–83) was added 288 mg of 55% NaH in mineral oil. After evolution of gas had ceased, the brown suspension was stirred at room temperature for 24 h. Another 288 mg of 55% NaH in mineral oil was added and the mixture was stirred at 60° C. for 18 h. The mixture was cooled, diluted with 50 ml of 10% aqueous citric acid and extracted 4 times with 50 ml of ethyl acetate. The combined organic phases were washed with water, dried over MgSO$_4$ and evaporated. The crude product was purified by column chromatography on silica gel eluting with hexane:ethyl acetate 1:1 and precipitated from diethyl ether to give 213 mg of 4-tert.-butyl-N-[6-(4-methoxy-2-butynyloxy)-5-(p-tolyl)-4-pyrimidinyl]-benzene sulfonamide as a white powder. LC-MS: $t_R$=5.61 min, [M+1]$^+$=480.30, [M−1]$^-$=478.39.

Example 96

To a mixture of 282 mg of 4-tert.-butyl-N-[6-chloro-5-(p-tolyl)4-pyrimidinyl]-benzene sulfonamide (Example 12c) and 1.10 g of 4-phenoxy-2-butyn-1-ol (prepared starting from phenyl-propargylether and para-formaldehyde following the procedure given in J. Chem. Soc. Perkin Trans. 1, 1991, 1721–1727) in 15 ml THF was added 271 mg of 55% NaH in mineral oil. The suspension was stirred for 4 h at reflux. The reaction mixture was cooled, diluted with 100 ml 10% aqueous citric acid and extracted 4 times with 50 ml of ethyl acetate. The combined organic phases were washed with water, dried over MgSO$_4$ and evaporated. The crude product was purified by column chromatography on silica gel eluting with heptane:ethyl acetate 1:1 and precipitated from diethyl ether to give 151 mg of 4-tert.-butyl-N-[6-(4-phenoxy-2-butynyloxy)-5-(p-tolyl)$_4$-pyrimidinyl]-benzene sulfonamide as a white powder. LC-MS: $t_R$=6.34 min, [M+1]$^+$=542.48, [M−1]$^-$=540.15.

What is claimed is:

1. A compound of the formula I:

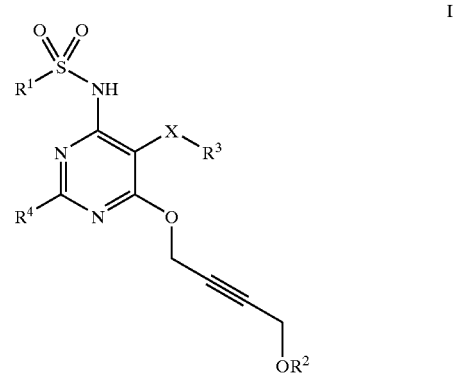

wherein

R$^1$ represents phenyl; mono-, di- or tri-substituted phenyl substituted with halogen, lower alkyl, lower alkenyl, lower alkenyl, lower alkoxy, hydroxy-lower alkyl, hydroxy-lower alkenyl, hydroxy-lower alkynl, trifluoromethyl, cycloalkyl, or hydroxy-cycloalkyl; 2-pyridyl; 5-substituted 2-pyridyl substituted with lower alkyl; or a five-membered heteroaryl ring containing one or two nitrogen, sulfur or oxygen atoms;

R$^1$ represents hydrogen; lower alkyl; phenyl; mono-, di- or tri-substituted phenyl substituted with halogen, lower alkyl, lower alkoxy, lower alkyloxy-lower alkyl, or trifluoromethyl; or a five-membered heteroaryl ring contatining one or two nitrogen, sulfur or oxygen atoms and which may be mono- or di-substituted with halogen, lower alkyl, lower alkoxy, or tirfluoromethyl, 2-pyrimidyl; mono- or di-substituted 2-pyrimidyl substituted with lower alkyl, lower alkoxy, halogen, or trifluoromethyl; or a group of the formula, —C(A)—B—R$^a$, wherein A represents O or S;

B represents NH; and

R$^a$ represents lower alkyl; cycloalkyl; phenyl; mono-, di- or tri-substituted phenyl substituted with halogen, lower alkyl, lower alkenyl, lower alkoxy, or trifluoromethyl; or a six-membered heteroaryl ring containing one or two nitrogen atoms and which may be mono- or di-substituted with halogen, lower alkyl, or lower alkyloxy;

$R^3$ represents phenyl; mono-, di- or tri-substituted with lower alkyl, lower alkenyl, lower alkyloxy, trifluoromethyl, halogen, or hydroxy;

$R^4$ represents hydrogen, halogen, trifluoromethyl, lower alkyl, lower alkyloxy, lower alkylthio, lower alkyloxy-lower alkyl; phenyl; mono- or di-substituted phenyl substituted with halogen, lower alkyl, lower alkoxy, lower alkylene or lower alkenylene or lower alkylenoxy or lower alklenedioxy forming with the phenyl ring a five- or six-membered ring; heteroaryl; or heterocyclyl; and X represents oxygen; sulfur; or a bond; and pure enantiomers, enantiomerically pure diastereomers, mixtures of diastereomers, diastereomeric recemates, mixtures of diastereomeric racemates and pharmaceutically acceptable salts thereof.

2. The compounds according to claim 1, wherein $R^3$ represents phenyl; mono-substituted phenyl substituted with lower alkyl, lower alkyloxy, trifluoromethyl, or halogen; and X represents oxygen or a single bond, and pharmaceutically acceptable salts thereof.

3. A compounds of formula II:

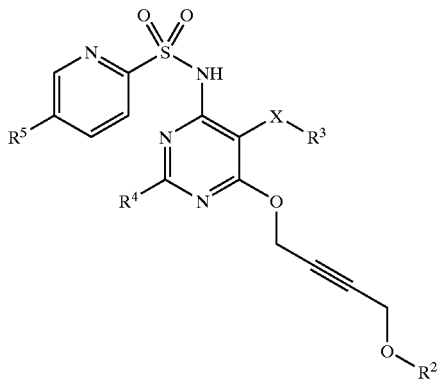

II wherein $R^2$ represents hydrogen; lower alkyl; phenyl; mono-, di- or tri-substituted phenyl substituted with halogen, lower alkyl, lower alkoxy, lower alkyloxy-lower alkyl, or trifluoromethyl; or a five-membered heteroaryl ring containing one or two nitrogen, sulfur or oxygen atoms and which may be mono- or di-substituted with halogen, lower alkyl, or lower alkoxy; benzyl; mono- or di-substituted benzyl substituted with halogen, lower alkyl, lower alkyl, or trifluoromethyl, 2-pyrimidyl; mono- or di-substituted 2-pyrimidyl substituted with lower alkyl, lower alkoxy, halogen, or trifluoromethyl; or a group of the formula, —C(A)—B—$R^a$, wherein A represents O or S;

B represents NH; and $R^a$ represents lower alkyl; cycloalkyl; phenyl; mono-, di- or tri-substituted phenyl substituted with halogen, lower alkyl, lower alkenyl, lower alkoxy, or trifluoromethyl; or a six-membered heteroaryl ring containing one or two nitrogen atoms and which may be mono- or di-substituted with halogen, lower alkyl, or lower alkyloxy;

$R^4$ represent hydrogen, halogen, trifluoromethyl, lower alkyloxy, lower alkylthio, lower alkyloxy-lower alkyl; phenyl; mono- or di-substituted phenyl substituted with halogen, lower alkyl, lower alkoxy, lower alkylene or lower alkenylene or lower alkylenoxy or lower alkylenedioxy forming with the phenyl ring a five- or six-membered ring; heteroaryl; or heterocyclycl; and X represents oxygen; sulfur; or a bond; and $R^5$ represents lower alkyl, and pharmaceutically acceptable salts of compounds of formula II.

4. A compound of formula III:

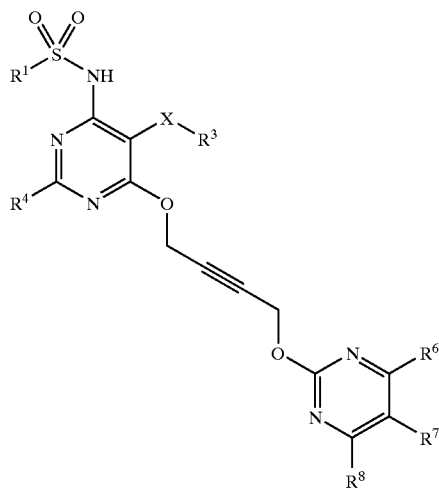

III wherein $R^1$ represents phenyl; mono-, di- or tri-substituted phenyl substituted with halogen, lower alkyl, lower alkenyl, lower alkynyl, lower alkoxy, hydroxy-lower alkyl, hydroxy-lower alkenyl, hydroxy-lower alkynyl, trifluoromethyl, cycloalkyl, or hydroxy-cycloalkyl; 2-pyridyl; 5-substituted 2-pyridyl substituted with lower alkyl; or a five-member heteroaryl ring containing one or two nitrogen, sulfur oxygen atoms;

$R^3$ represents phenyl; mono-, di- or tri-substituted phenyl substituted with lower alkyl, lower alkenyl, lower alkyloxy, trifluoromethyl, halogen, or hydroxy;

$R^4$ represents hydrogen, halogen, trifluoromethyl, lower alkyl, lower alkyloxy, lower alkylthio, lower alkyloxy-lower alkyl; phenyl; mono- or di-substituted phenyl substituted with halogen, lower alkyl, lower alkoxy, lower alkylene or lower alkenylene or lower alkylenoxy or lower alkylenedioxy forming with the phenyl ring a five- or six-membered ring; heteroaryl; or heterocyclyl; and X represent oxygen; sulfur; or a bond; and $R^6$, $R^7$, and $R^8$, each and independently represents hydrogen, lower alkyl, lower alkyloxy, halogen, or trifluoromethyl; and pharmaceutically acceptable salts thereof.

5. A compound of formula IV:

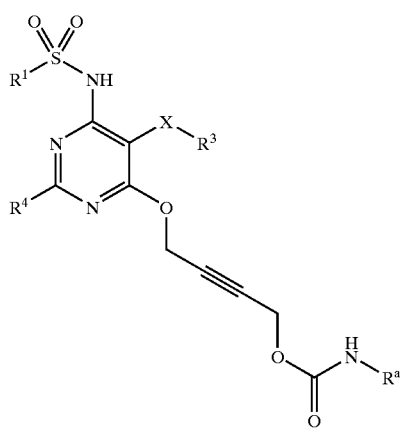

wherein
- R¹ represents phenyl; mono-, di- or tri-substituted phenyl substituted with halogen, lower alkyl, lower alkenyl, lower alkynyl, lower alkoxy, hydroxy-lower alkyl, hydroxy-lower alkenyl, hydroxy-lower alkynyl, trifluoromethyl, cycloalkyl, or hydroxy-cycloalkyl; 2-pyridyl; 5-substituted 2-pyridyl substituted with lower alkyl; or a five-membered heteroaryl ring containing one or two nitrogen, sulfur or oxygen atoms;
- $R^a$ represents lower alkyl; cycloalkyl; phenyl; mono-, di- or tri-substituted phenyl substituted with halogen, lower alkyl, lower alkenyl, lower alkoxy, or trifluoromethyl; or a six-membered heteroaryl ring containing one or two nitrogen atoms and which may be mono- or di-substituted with halogen, lower alkyl, or lower alkyloxy;
- R³ represents phenyl; mono-, di- or tri-substituted phenyl substituted with lower alkyl, lower alkenyl, lower alkyloxy, trifluoromethyl, halogen, or hydroxy;
- R⁴ represents hydrogen, trifluoromethyl, lower alkyl, lower alkyloxy, lower alkylthio, lower alkyloxy-lower alkyl; phenyl; mono- or di-substituted phenyl substituted with halogen, lower alkyl, lower alkoxy, lower alkylene or lower alkenylene or lower alkylenoxy or lower alklenedioxy forming with the phenyl ring a five- or six-membered ring; heteroaryl; or heterocyclyl; and
- X represents oxygen; sulfur; or a bond; and
pharmaceutically acceptable salts thereof.

6. The compound according to claim 1, wherein R² represents lower alkyl, and
pharmaceutically acceptable salts thereof.

7. A compound selected from:
5-isopropyl-N-[6-(4-hydroxy-2-butynyloxy)-5-(o-methoxyphenoxy)-2-(4-pyridyl)-4-pyrimidinyl]-2-pyridine sulfonamide;
4-tert.-butyl-N-[6-(4-hydroxy-2-butynyloxy)-5-(o-methoxyphenoxy)-2-(4-pyridyl)-4-pyrimidinyl]-benzene sulfonamide;
5-methyl-N-[6-(4-hydroxy-2-butynyloxy)-5-(o-methoxyphenoxy)-2-(4-pyridyl)4-pyrimidinyl]-2-pyridine sulfonamide;
5-isopropyl-N-[6-chloro-5-(o-methoxyphenoxy)-2-(2-pyrimidinyl)-4-pyrimidinyl]-2-pyridine sulfonamide;
4-tert.-butyl-N-[6-chloro-5-(o-methoxyphenoxy)-2-(2-pyrimidinyl)-4-pyrimidinyl]benzene sulfonamide;
5-isopropyl-N-[6-(4-hydroxy-2-butynyloxy)-5-(o-methoxyphenoxy)-2-(N-morpholino)-4-pyrimidinyl]-2-pyridine sulfonamide;
5-isopropyl-N-[6-(4-hydroxy-2-butynyloxy)-5-(p-tolyl)-2-(4-pyridyl)-4-pyrimidinyl]-2-pyridine sulfonamide;
5-isopropyl-N-[6-(4-(4,6-dimethoxy-2-pyrimidinyloxy)-2-butynyloxy)-5-(o-methoxyphenoxy)-2-(4-pyridyl)-4-pyrimidinyl]-2-pyridine sulfonamide;
4-tert.-butyl-N-[6-(4-(2-pyrimidinyloxy)-2-butynyloxy)-5-(o-methoxyphenoxy)-2-(4-pyridyl)-4-pyrimidinyl]-benzene sulfonamide;
4-tert.-butyl-N-[6-(4-(4,6-dimethoxy-2-pyrimidinyloxy)-2-butynyloxy)-5-(o-methoxyphenoxy)-2-(4-pyridyl)-4-pyrimidinyl]-benzene sulfonamide;
2-pyridinyl-carbamic acid 4-[6-(5-isopropyl-pyridine-2-sulfonylamino)-5-(2-methoxy-phenoxy)-2-pyridin-4-yl-pyrimidin-4-yloxy]-but-2-ynyl ester;
phenyl-carbamic acid 4-[6-(5-isopropyl-pyridine-2-sulfonylamino)-5-(2-methoxy-phenoxy)-2-morpholin-4-yl-pyrimidin-4-yloxy]-but-2-ynyl ester;
2-pyridinyl-carbamic acid 4-[6-(5-isopropyl-pyridine-2-sulfonylamino)-5-(2-methoxy-phenoxy)-2-(N-morpholino)-pyrimidin-4-yloxy]-but-2-ynyl ester;
2-pyridinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester;
4-pyrazinyl-carbamic acid 4-[6-(5-methyl-pyridine-2-sulfonylamino)-5-(2-methoxy-phenoxy)-2-(4-morpholino)-pyrimidin-4-yloxy]-but-2-ynyl ester;
4-tert.-butyl-N-[6-(4-methoxy-2-butynyloxy)-5-(o-methoxyphenoxy)-2-(2-pyrimidinyl)-4-pyrimidinyl] benzene sulfonamide; or
5-isopropyl-N-[6-(4-methoxy-2-butynyloxy)-5-(o-methoxyphenoxy)-2-(N-morpholino)-4-pyrimidinyl]-2-pyridine sulfonamide.

8. A pharmaceutical composition comprising a compound of any one of claims 1 to 7 and a pharmaceutically acceptable carrier and/or adjuvant.

9. A method for treating a subject with disorders which are associated with a role of endothelin comprising administering the compound according to any one of claims 1 to 7.

10. A process for the manufacture of pharmaceutical compositions for the treatment of disorders associated with a role of endothelin containing one or more compounds as claimed in any one of claims 1 to 7 as active ingredients, which process comprises mixing one or more active ingredients with a pharmaceutically acceptable excipient.

* * * * *